(12) United States Patent
Jack et al.

(10) Patent No.: US 6,660,475 B2
(45) Date of Patent: Dec. 9, 2003

(54) USE OF SITE-SPECIFIC NICKING ENDONUCLEASES TO CREATE SINGLE-STRANDED REGIONS AND APPLICATIONS THEREOF

(75) Inventors: William E. Jack, Wenham, MA (US); Ira Schildkraut, Cerrillos, NM (US); Julie Forney Menin, Newburyport, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/738,444

(22) Filed: Dec. 15, 2000

(65) Prior Publication Data

US 2003/0022317 A1 Jan. 30, 2003

(51) Int. Cl.[7] .......................... C12Q 1/68; C12P 19/34; G01N 33/00; C07H 21/02; C07H 21/04

(52) U.S. Cl. .......................... 435/6; 435/91.1; 436/94; 536/23.1; 536/24.3; 536/24.33

(58) Field of Search .......................... 435/6, 91.1, 91.2, 435/183; 436/94, 501; 536/23.1, 24.3, 24.33, 25.3

(56) References Cited

U.S. PATENT DOCUMENTS

| | | | |
|---|---|---|---|
| 5,137,824 A | | 8/1992 | Murakami et al. |
| 5,229,283 A | | 7/1993 | Berninger |
| 5,786,195 A | * | 7/1998 | Xu et al. .................... 435/199 |

FOREIGN PATENT DOCUMENTS

| | | |
|---|---|---|
| CA | 2088766 | 6/1992 |
| EP | 544894 | 6/1992 |
| EP | 1 176 204 | 6/2001 |
| WO | WO 92/22649 | 12/1992 |

OTHER PUBLICATIONS

Alland et al., Identification of differentially expressed mRNA in prokaryotic organisms by customized amplification libraries (DECAL) . Proc. Natl. Acad, Sci. USA, 95, 13227–13232, Oct. 1998.*
Wang et al., Preparation of DNA substrates for in Vitro mismatch repair. Molecular Biotechnology, 15, 97–104, Jun. 2000.*
New England Biolabs 96/97 Catalog, pp. 13, 17, 36, 43, 53, and 54. Published by New England Biolabs, Inc., 32 Tozer Road, Beverly, MA 01915-5599.*
Higashitani et al., Multiple DNA comformational changes induced by an initiiator protein precede the nicking reaction in a rolling circle replication orgin. J. Mol. Biol., 237, 388–400, 1994.*
The NEB Transcript 6, 7 (1994).
Abdurashitov, et al., Mol. Biol. (Mosk) 30:1261–1267 (1996).
Aslanidis and de Jong, Nucl. Acids Res. 18:6069–6074 (1990).

(List continued on next page.)

*Primary Examiner*—Gary Benzion
*Assistant Examiner*—Frank W Lu
(74) *Attorney, Agent, or Firm*—Gregory D. Williams; Harriet M. Strimpel

(57) ABSTRACT

The present invention relates to the use of site-specific nucleic acid nicking enzymes to create single-stranded regions in duplex nucleic acids. Such single-stranded regions can take the form of gaps interior to the duplex, or terminal single-stranded regions. Single-stranded termini can be crafted to allow linkage of various elements via base-pairing with elements containing a complementary single-stranded region. This joining is useful, for example, in an ordered, oriented assembly of DNA modules to create cloning or expression vectors. This joining is also useful in attaching detection probes and purifying DNA molecules containing the single-stranded region. Gaps are useful in similar applications, including attaching detection or purification probes.

7 Claims, 10 Drawing Sheets

OTHER PUBLICATIONS

Bitinaite, et al., Proc. Natl. Acad. Sci. USA 95:10570–10575 (1998).
Chan, et al., Nucl. Acids Res. 19:353–358 (1991).
Dietmaier, et al., Nucleic Acids Res. 21:3603–3604 (1993).
Higashitani, et al., J. Mol. Biol. 237:388–400 (1994).
Jeltsch, et al., Trends in Biotechnology 14:235–238 (1996).
Li and Evans, Nucleic Acids Res. 25:4165–4166 (1997).
Modrich and Zabel, J. Biol. Chem. 251:5866–5874 (1976).
Needleman and Wunsch, J. Mol. Biol. 48:443–453 (1970).
Nisson, et al. PCR Methods Appl. 1:120–123 (1991).
Rubin, et al., Nucleic Acids Res. 4:1803–1813 (1977).
Rubin and Modrich, Nucleic Acids. Res. 5:2991–2997 (1978).
Stahl, et al., Proc. Natl. Acad. Sci. USA 93:6175–6180 (1996).
Taylor, et al., Nucl. Acids Res. 13:8765–8785 (1985).
Taylor, et al., Nuc. Acids Res. 13:8749–8764 (1985).
Tillett and Nelian, Nucl. Acids Res. 27:e26 (1999).
Walker, et al., Proc. Natl. Acad. Sci. USA 89:392–396 (1992).
Waugh and Sauer, Proc. Natl. Acad. Sic. USA 90:9596–9600 (1993).
Zhou and Hatahet, Nucl. Acids Res. USA 23:1089–1090 (1995).
Zoller and Smith, DNA 3:479–488 (1984).

* cited by examiner

GAP FORMATION

COHESIVE TERMINI FORMATION

CREATION OF 5' COHESIVE ENDS

CREATION OF 3' COHESIVE ENDS

GAP CREATION

DETECTION

ASSEMBLY

BRANCHED STRUCTURES

PURIFICATION

USE OF SITE-SPECIFIC NICKING ENDONUCLEASES TO CREATE SINGLE-STRANDED REGIONS AND APPLICATIONS THEREOF

BACKGROUND OF THE INVENTION

The joining of DNA fragments is central to the methodology of molecular biology. There is a consistent need to efficiently join DNA segments to form useful, informative arrays that can allow for analysis in vitro and in vivo. DNA restriction endonucleases, in combination with DNA ligase, have been the principal tools used to create such fragment arrays. This approach relies heavily upon the natural occurrence of appropriate restriction endonuclease recognition sites, and to a lesser extent on being able to insert appropriate sites through such techniques as site-directed mutagenesis, PCR or linker insertion.

The primary method of joining DNA fragments involves enzymatic ligation, preferably with cohesive termini created by restriction endonuclease cleavage such that the two fragments can only be joined in a single orientation. Often, the product of that ligation is a circular molecule suitable for transformation into and propagation in a bacterial host. Alternatively, the cohesive termini may be identical, in which case two possible orientations can result, necessitating screening of the final products. Finally, one or both of the termini may be blunt ends, reducing the efficiency of ligase joining, but also eliminating the requirement for compatible cohesive termini. In a practical sense, the number of elements that can be joined is limited to two, possibly three elements. In addition, in the absence of DNA ligase, no joining is observed.

One naturally-occurring method that increases the efficiency of fragment joining is observed in the life cycle of the bacteriophage lambda. Upon lambda infection, a linear double-stranded genome enters the cell. This genome is circularized prior to replication via pairing of complementary 12-nucleotide single-stranded regions at the two ends of the genome. These single-stranded regions are created after replication and prior to phage packaging by the action of the lambda int gene product. The int gene product can be used in vitro in much the same way as restriction endonucleases to cut and rejoin DNA fragments. In theory, this approach could be expanded to join multiple elements in a defined, ordered array. However, this would require multiple int-like proteins that recognize different sequences to assure unique orientation of fragments. This could be accomplished by using similar regions from different bacteriophages (e.g., bacteriophage P22), but this would require the isolation of a separate int gene product for each set of cohesive ends, and potentially introduce difficulties in optimizing reaction conditions for more than one cleavage. Additionally, in this approach the cohesive sequence is constrained to the naturally occurring sequence. Thus, while this is a possible approach, it is not the optimal approach.

An alternative is to create single-stranded regions by the combined action of nucleases. Several methodologies have been described, including: limiting digestion by controlling the time of digestion (Li and Evans *Nucleic Acids Res.* 15:4165–4166 (1997)), inhibiting digestion at a selected location (Aslanidis and de Jong *Nucleic Acids Res.* 18:6069–6074 (1990); Zhou and Hatahet *Nucleic Acids Res.* 23:1089–1090 (1995); Dietmaier, et al. *Nucleic Acids Res.* 21:3603–3604 (1993)) and selectively enhancing digestion at a specific location (U.S. Pat. No. 5,137,814; Nisson et al. *PCR Methods Appl.* 1:20–123 (1991)). In still another method, a mixture of staggered PCR products are hybridized together to create overhangs (Tillett and Nelian *Nucleic Acids Res.* 27: e26 (1999)). Most of these methods require a PCR step to add a DNA sequence element or non-standard nucleotide to the termini as a prelude to exonuclease action. The inherent infidelity of PCR raises concerns of introducing a mutation into the amplified DNA sequence, thus it would be more desirable to assemble DNA fragments replicated in vivo. Furthermore, it is difficult to assess whether the desired enzymatic action has been completed on the DNA termini since the gross properties of the fragment (e.g., electrophoretic mobility) are largely unaltered.

SUMMARY OF THE INVENTION

The present invention is related to the production of defined single-stranded regions in DNA, and the use of such regions to join, detect and purify such molecules. Site-specific DNA nicking endonucleases are used to form the single-stranded regions by nicking at the boundaries of the single-strand regions, either on opposing DNA strands (creating terminal single-stranded regions) or on the same strand (creating a single-strand gap).

Creation of such single-stranded regions facilitates assembly of multiple nucleic acid fragments in an ordered array, either linear or circular. This is useful in a variety of applications, including construction of vectors with interchangeable cassettes. Although the examples provided here use the enzyme N.BstNBI, the skilled artisan will appreciate that any other site-specific nicking enzyme would give equivalent results.

---

OLIGONUCLEOTIDE SEQUENCES

216-113 (SEQ ID NO:1)
pAAATCAATCTAAAGTATATACCGGTAAACTTGGTCTGACA 216-114 (SEQ ID NO:2)
pCTAGCATTAGTCAGACTCTACATTCAAATATGTATCCG

-continued

OLIGONUCLEOTIDE SEQUENCES 216-117 (SEQ ID NO:3)
pGCGCTCGATGTCAGACTCGAGCAAAAGGCCAGCAAAAG 216-112 (SEQ ID NO:4)
pGAGTCCGATTGACCTAAGCGGATACTCTGACGACTCGTAGAAAAGA
TCAAAGGATC 222-14 (SEQ ID NO:5)
pGAGTCTCAGACTATCTGGAGCGACTGACTCAAACTTGGTCTGACAG
TTACC 241-83 (SEQ ID NO:6)
GTAAATATCGGACTCTACAATCAAATATGTATCCGCTCAT 226-10 (SEQ ID NO:7)
GATCGAGTCTGACATCGAGCGCCTAGCATTAGTCAGACTCGATATCG
AGTCTCAGCCTGTTAGCGATGGTACATGACGACTC 226-11 (SEQ ID NO:8)
CTAGGAGTCGTCATGTACCATCGCTAACAGGCTGAGACTCGATATCG
AGTCTGACTAATGCTAGGCGCTCGATGTCAGACTC 226-180 (SEQ ID NO:9)
CATGTCTAGACTGCAGAGATCT 226-181 (SEQ ID NO:10)
AGATCTCTGCAGTCTAGA 235-262 (SEQ ID NO:11)
TACATTCAAATATGTATCCGC 235-263 (SEQ ID NO:12)
TAAACTTGGTCTGACAGTTAC 236-184 (SEQ ID NO:13)
GAGTATCCGCTTAGGTCAATCGGACTCGGACCGGATATCACATGTGA
GTCGTCA 236-185 (SEQ ID NO:14)
CCTGTTAGCGATGGTACATGACGACTCACATGTGATATCCGGTCCGA
GTCCGAT 242-11 (SEQ ID NO:33)
pGAGTCAGCTCAATGTTGCCAGTCAGGACTCGTAGAAAAGATCAAAG
GATC 242-12 (SEQ ID NO:34)
pGGGCCACGTAGACTCGAGCAAAAGGCCAGCAAAAG 244-114 (SEQ ID NO:50)
CTGGCAACATTGATCGGACTCGGACCGGATATCACATGTGAGTCGTCA 244-115 (SEQ ID NO:51)
GCTCCAGATAGTTGACGACTCACATGTGATATCCGGTCCGAGTCCGAT

DETAILED DESCRIPTION OF THE INVENTION

The present invention is directed to creation of defined single-stranded regions in DNA using site-specific endonucleases that predominantly cleave only one strand of the DNA duplex (nicking endonucleases) at defined locations. In one embodiment, DNA substrates are designed such that the nicking endonuclease(s) makes at least two nicks in duplex DNA. By positioning the sites of these nicks close together, the region bounded by the nicks in duplex DNA becomes susceptible to dissociation, creating single-stranded regions defined by the cleavage sites. The cleavage sites are in turn defined by the position of the nicking enzyme recognition site and the disposition of the nicking site relative to that recognition site.

Figure 1A:
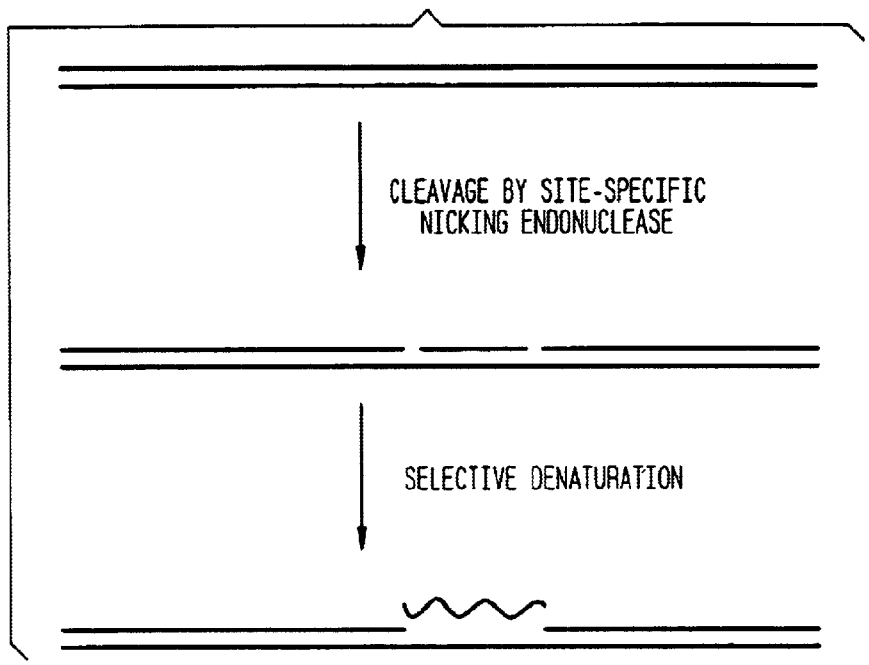
FIG. 1: Overview of sequence-specific single strand formation using site-specific nicking endonucleases.
Figure 1B:
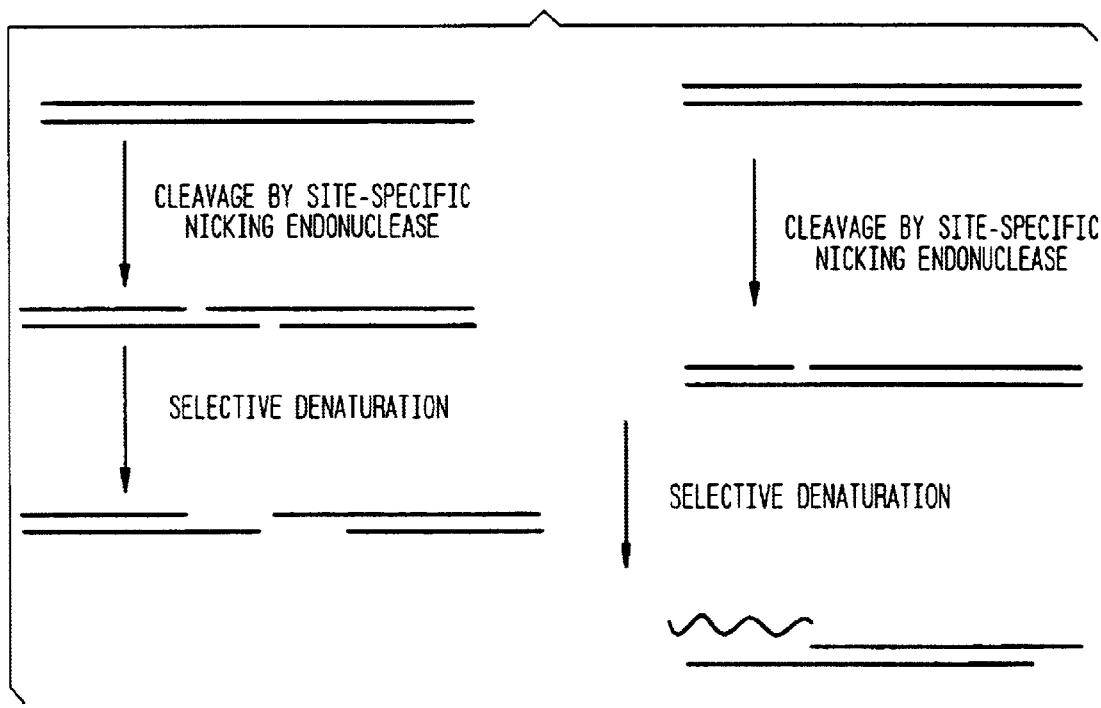

If the nicking sites occur on the same strand of the DNA duplex, a single-stranded gap can be created (FIG. 1). If the nicking sites occur on opposite strands of the DNA duplex, dissociation of the strands will create complementary single-stranded termini. As described below, both types of single-stranded regions can be useful in a variety of applications.

Examples of Nicking Endonucleases

Several types of endonucleases can be envisioned in the context of the present invention. The basic requirement is that the enzyme cleave in a site- and strand-specific fashion, acting predominantly on one strand of the duplex DNA.

Nicking endonuclease activity has been described for some traditional restriction endonucleases. For example, EcoRI endonuclease has been observed to nick one strand of its recognition sequence, dissociate and rebind to cleave the other strand, depending on the substrate and reaction conditions (Modrich and Zabel, *J. Biol. Chem.* 251:5866–5874 (1976); Ruben, et al., *Nucleic Acids Res.* 4:1803–1813 (1977); Rubin and Modrich, *Nucleic Acids Res.* 5:2991–2997 (1978)). However, there is no known strand specificity for the nicking, a possible consequence of the symmetry of the recognition site. Additionally, cleavage of the second strand of the nicked recognition site occurs with similar kinetics as cleavage of the first strand, eventually converting all nicked sites to double-strand cleavages. Thus, while this class of enzyme could produce nicked species for use in the present invention, such enzymes are not the preferred enzymes.

Proposals have been tendered for conversion of double-stranded endonucleases into enzymes that can cut only a single strand of the DNA duplex (e.g., Waugh and Sauer, *Proc. Nat. Acad. Sci. USA* 90:9596–9600 (1993); Jeltsch, et al., *Trends Biotechnol.* 14:235–238 (1996)). Enzymes so converted continue to recognize a specific sequence, but cleave only one strand, or predominantly one strand of duplex DNA. For those enzymes with symmetric recognition sequences, this class of altered enzymes would suffer from the same limitations as described above for restriction endonucleases. However, if enzymes with asymmetric recognition sequences can be induced to nick predominantly or entirely in one strand such enzymes would be useful in the present invention. Conversion of restriction endonucleases into site-specific nicking enzymes has been described (Stahl, et al., *Proc. Natl. Acad. Sci. USA* 93:6175–6180 (1996); Bitinaite, et al., *Proc. Natl. Acad. Sci. USA* 95:10570–10575 (1998)). However, these references do not describe the use of such enzymes in the creation of single-stranded regions.

Chemical modification of the DNA substrate has been used to limit restriction endonuclease action to site- and strand-specific nicking. For example, restriction endonucleases have been identified that nick at recognition sites in which one of the scissile phosphodiester bonds has been replaced by a phosphorothioate linkage (Taylor, et al., *Nucleic Acids Res.*, 13:8749–8764 (1985)). This methodology has been used in conjunction with exonuclease III digestion to create large, primarily random regions for oligonucleotide-directed mutagenesis (Taylor, et al., *Nucleic Acids Res.* 13:8765–8785 (1985)) and to create polymerase entry sites in strand displacement amplification (Walker, et al., *Proc. Natl. Acad. Sci. USA* 89:392–396 (1992)), but not to create single-stranded regions with specific borders as provided in the present invention. However, with appropriate positioning of the phosphorothioate linkages, and judicious selection of restriction endonucleases, nicks could potentially be introduced allowing implementation of the present invention. However, this is not the preferred way to practice the present invention due to the added step of introducing the phosphorothioate linkage.

Elements of replication machinery with site-specific nicking activity have also been described. For example, Horiuchi, et. al. have studied the nicking reaction catalyzed by the filamentous bacteriophage f1 gpII, a reaction that is involved in initiation of rolling circle DNA replication of the phage genome (Higashitani, et al., *J. Mol. Biol.* 237:388–400 (1994)). As such, the site- and strand-specific nicking properties of this enzyme could potentially be harnessed for use in the present invention.

While the above described enzymes and methods for introducing a site- and strand-specific nick in duplex DNA can be exploited in the present invention, a more preferred nicking enzyme is exemplified by N.BstNBI endonuclease (New England Biolabs, Beverly, Mass.) or its isoschizomer N.BstSEI (Abdurashitov, et al., *Mol. Biol.* (Mosk) 30:1261–1267 (1996)). These enzymes have characteristics of being elements of restriction modification systems, namely the endonuclease is accompanied by a site-specific methyl transferase that modifies the recognition sequence and blocks cleavage by the endonuclease. The recognition site for N.BstNBI is:

```
5'...GAGTCNNNN▽N...3'     (SEQ ID NO:15)
3'...CTCAGNNNN N...5'
``` where the cleavage site is indicated by "▽" and N indicates any base (subject to the normal rules of base pairing between the strands). Importantly, the N.BstNBI recognition sequence is asymmetric, otherwise no strand bias would be expected.

By analogy with the wide variety of restriction endonucleases that have been discovered and characterized, a reasonable expectation is that additional nicking enzymes of this type will be identified, some of which will act on different recognition sequences. Site-specific nicking endonucleases can be identified during routine screening for restriction endonucleases, as was N.BstNBI. This identification relies on the occurrence of two closely-disposed recognition sites, each site directing nicking on opposite strands of the DNA substrate. In such an arrangement, a double-strand cleavage event is scored. Determination of the sites of cleavage, combined with analysis of the sequences surrounding the cleavage sites, allows a determination of the recognition site for the cleavage activity. Because restriction endonuclease cleavage sites generally leave no more than a 4-nucleotide cohesive end, traditional screening does not need to take steps to promote dissociation of cohesive ends. Thus, site-specific nicking endonucleases are only identified in this methodology when sites are close enough to produce short cohesive ends. Identification may be improved by post-cleavage treatment of the DNA to promote dissociation of longer cohesive ends, such as heating the sample to 65° C. prior to gel analysis. Newly-identified site-specific nicking endonucleases may cut to one side of the recognition site, as with N.BstNBI, or possibly internal to the recognition sequence. Both of these types of nicking enzymes would be functional in the present invention by correctly disposing the corresponding nicking enzyme recognition site about the target region.

Figure 2A:
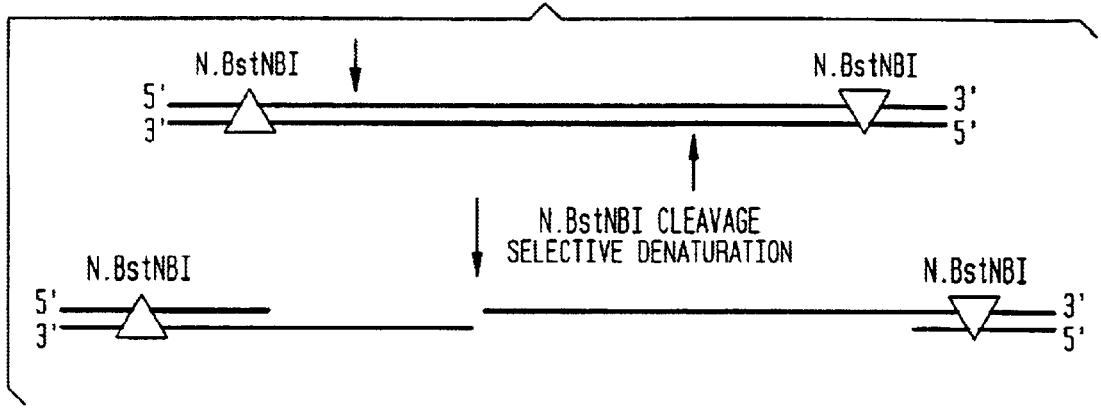
FIG. 2: Use of N.BstNBI to create 5' and 3' cohesive ends and single-stranded gaps.
Figure 2B:
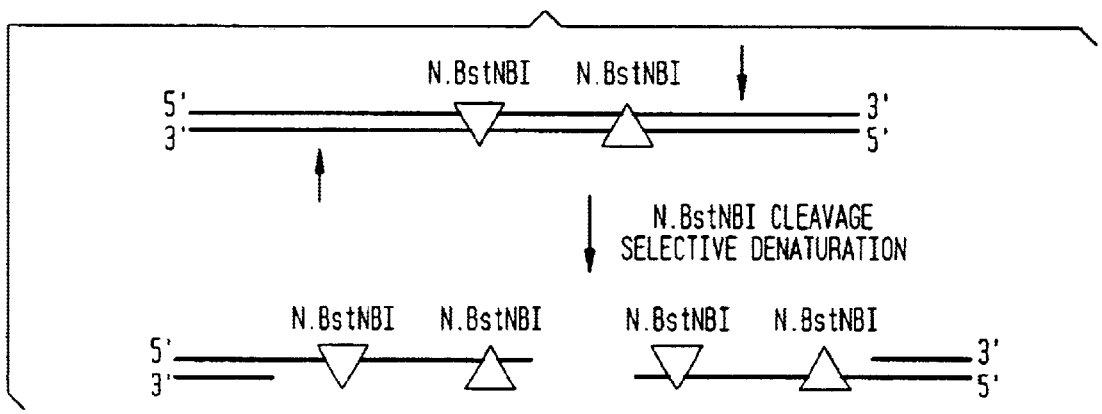
Figure 2C:
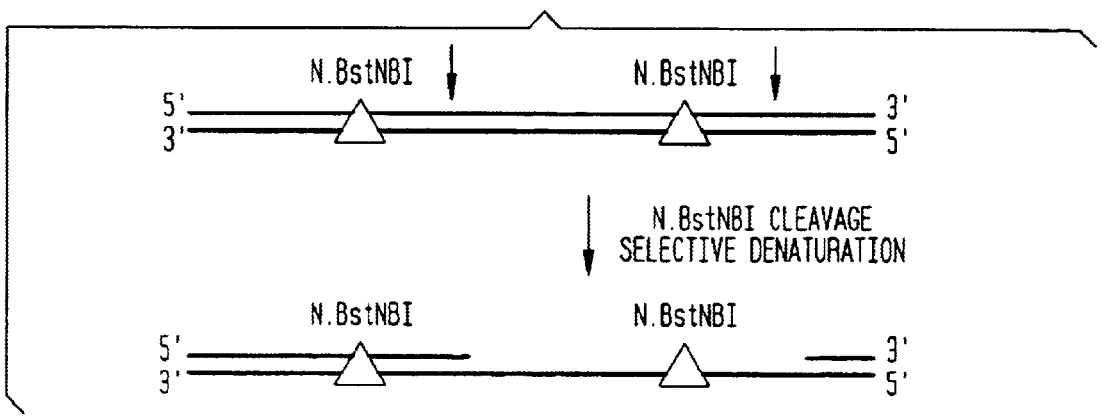
Figure 3A:
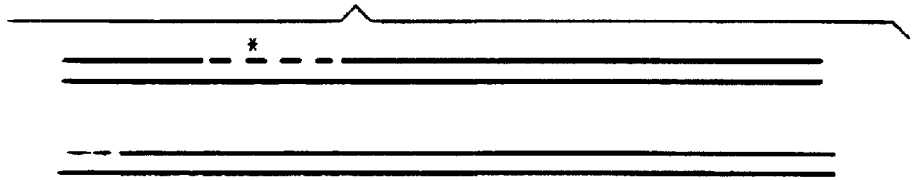
FIG. 3: Examples of applications using DNA molecules with single-stranded regions.
Figure 3B:
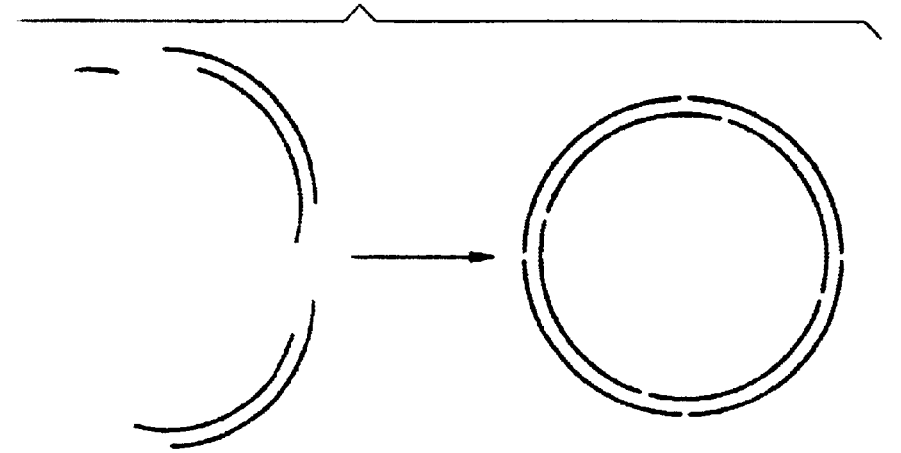
Figure 3C:
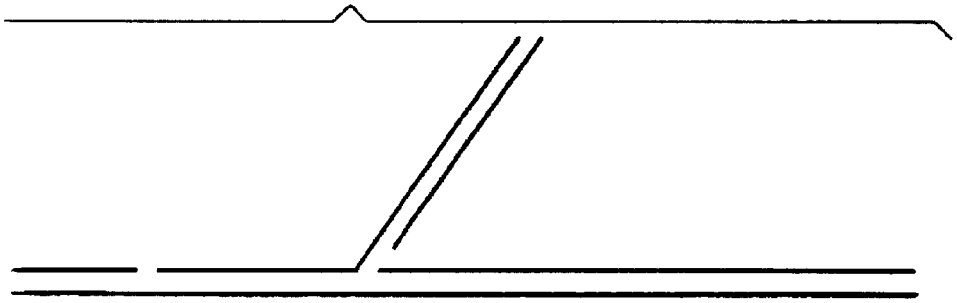
Figure 3D:
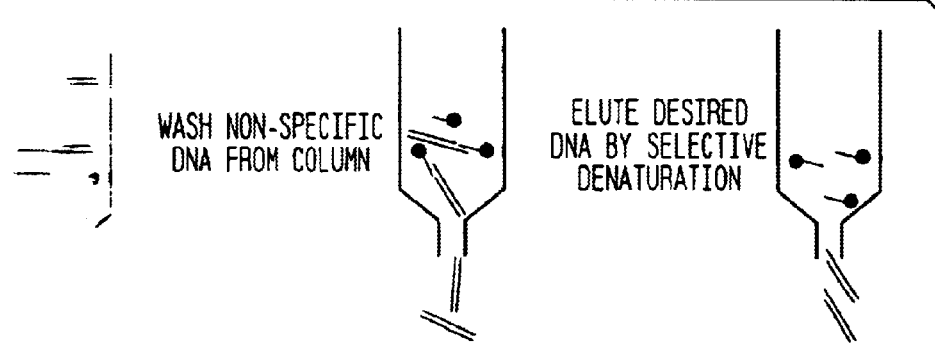

The Disposition of Nicking Sites Determines the Character of the Single-Stranded Region Placement of the nicking enzyme recognition sequence is a crucial element in determining the nature of the single-stranded region that is created. As discussed above, the disposition of nicking sites can give rise to single-stranded gaps or to cohesive termini. The use of site-specific nicking enzymes to produce those nicks necessitates placing the corresponding recognition sites near the nicking sites, placing restrictions on the sequences in and/or around the single-stranded region. The nature of these constraints is dictated by the disposition of the nicking site relative to the recognition site and on whether a gap or single-stranded termini is generated. For example, if the nicking site is internal to the recognition sequence, then elements of the recognition sequence inevitably reside in both the single-strand sequence created and in the flanking sequences. As a consequence, some flexibility is lost in designing unique cohesive termini. When, however, the nicking site is located outside the recognition sequence, three configurations are possible, each with desirable features. First, recognition sites can be oriented so that cleavage occurs between the two sites (FIG. 2a). As the recognition sites are outside of the single-stranded region, there are no a priori constraints on this region. Sequences on both sides of the cohesive termini are constrained to having the recognition sequence. Second, both sites can be oriented so that cleavage occurs exterior to the two sites (FIG. 2b). In this configuration the flanking sequences are not constrained, although the single-stranded region must include both of the two recognition sequences. Finally, both sites can be oriented in tandem, with one site within the single-stranded region and the other outside, with the net result being two nicks on the same strand (FIG. 2c). In this configuration, sequences to one side of and within the single-stranded region are constrained. The third arrangement will not produce cohesive ends, but rather a gapped single-strand portion of DNA.

While the illustration envisions using an enzyme that nicks to the 3' end of the recognition sequence, enzymes that cleave 5' of the recognition sequence should give similar results, with the difference being creation of 3' instead of 5' overhangs with the first scenario, and 5' instead of 3' overhangs with the second scenario.

Additionally, although the illustration displays the use of two cleavages to create the single-stranded regions, more nicking sites may be clustered to create multiple nicks on the same strand of the DNA duplex. This may be desirable, for example, to produce small single-strand fragments that will be more easily dissociated to expose gaps or single-strand termini.

The illustration also shows use of a single nicking enzyme to perform nicking reactions. Two separate nicking enzymes could also be appropriately mixed to generate a similar product. Alternatively, single-stranded termini could be created by introduction of a single nick near the terminus of a linear molecule, where the linear molecule either exists naturally, is a synthetic molecule, or is created by in vitro reactions such as, but not limited to, restriction endonuclease cleavage or the polymerase chain reaction (PCR).

The sequence of the single-strand cohesive ends can be defined by the user, as illustrated in the accompanying example. The distance between the nicking sites will determine the length of the cohesive region. For use in joining DNA fragments, the length of this region between nicks should be (1) long enough to allow unique, stable pairing between elements under the reaction conditions used in the joining reaction and (2) short enough to allow the single-stranded cohesive ends to be separated by denaturing forces that leave the rest of the DNA intact during the isolation steps preceding joining. The exact reaction conditions defined by these limitations depend, at least, on temperature, ionic strength, and DNA concentration. The examples illustrated below employ cohesive ends 12 or 18 nucleotides long, although lengths both shorter and longer are also in the scope of the present invention.

Design of Extended Single-Strand Cohesive Ends

One advantage of the described invention is the ability to design the sequence of the cohesive ends formed during the nicking reaction. While not absolutely required, ideally, these cohesive ends will be able to efficiently anneal only with their complements. Several characteristics are described to help ensure this pairing. The cohesive ends ideally:

1) Should have little propensity to form secondary structure. Secondary structure has the potential to create self-pairing that competes with the desired pairing with the complementary strand.

2) Should have minimal ability to form a complementary duplex with themselves or any of the cohesive ends in the assembly mixture other than the designed pair.

Other characteristics are also desirable, but not absolutely required, for the cohesive ends:

3) Have a GC content of about 50% to maximize the combinations possible and normalize the predicted melting temperature of the various annealed cohesive ends.

4) Lack restriction sites with recognition sites larger than 4 base pairs. This is a minor point that potentially gives more flexibility in having unique restriction sites in final constructs.

Many protocols could yield sequences that fit the above design criteria, including one briefly outlined below. The skilled artisan will appreciate that it is the design characteristics rather than rigid adherence to design protocols that is central to the present invention. For example, sequences do not necessarily need to be randomly generated and sequence alignments and secondary structure predictions can be fashioned using alternate software or manual manipulations.

1) Generate a random nucleotide sequence in which:
  a. $|G-C|=0$ or 1
  b. $|A-T|=0$ or 1
  c. $|(G+C)-(A+T)|=0$ or 1
where G, C, A and T represent the number of G, C, A and T residues, respectively.

2) Using the GCG (Genetics Computer Group, Inc., Madison, Wis.) software program foldRNA (Chan, et al., *Nucleic Acids Res.* 19:353–358 (1991)), check for potential secondary structure of the single strand. Bias selection to those with unfavorable folding energies.

3) Using the GCG program mapsort (Genetics Computer Group, Inc., Madison, Wis.), check for the occurrence of restriction sites, particularly those for the site-specific nicking endonuclease to be employed, or with recognition sequences longer than four nucleotides.

4) Using the GCG (Genetics Computer Group, Inc., Madison, Wis.) program GAP (Needleman and Wunsch, *J. Mol Biol.* 48:443–453 (1970)), check for self-hybridization and for predicted hybridization between all possible sets of single-strand ends (the sequence itself and its complement). Note the number of matched base pairs in the alignment, the number of consecutive base pairs, and the length of the gap between paired nucleotides. Also note whether the predicted pairing creates a nicked junction or a gap. Bias the selection to those with few matched base pairs, short patches of consecutive base pairs and with maximal gaps between paired nucleotides.

5) Select from the pool of generated sequences those that best fit the above criteria.

One possible limitation on this construction is the occurrence of recognition sites for the site-specific nicking endonuclease within the DNA fragment, thus producing nicks beyond those required to create the gaps or cohesive ends. Several approaches are possible to circumvent this limitation. (1) Sequence elements can be chosen that lack such sites. (2) Sites existing within the element can be eliminated by deletion or mutation. Where the site exists in coding regions, this mutation can be designed to be translationally silent, and thus not affect the coding capacity of the gene. (3) If the nicking sites are far enough apart, dissociation of the individual internal pieces can be restrained by choice of reaction conditions. The skilled artisan will recognize that these conditions will depend on the length of the single-stranded region and on the GC content within this region, in both cases relative to the portions of the DNA that will remain double-stranded following treatment. Parameters that promote single-strand formation include, but are not limited to, elevated temperatures, low ionic strength and alkaline pH. These parameters can be manipulated individually or in combination to give the desired result, namely dissociation of the single-stranded region without dissociation of the remaining portions of the DNA duplex. Appropriate conditions can be deduced by incrementally varying the above parameters and observing the nature of the products, for example by gel electrophoresis as described in the examples. The mildest conditions able to effect single-strand formation are preferable in the present invention. As such conditions are identified, nicks within the elements that are far enough apart will be transparent in the cloning protocols noted below. (4) Finally, as multiple nicking enzymes are identified, judicious choice of enzymes can reduce the potential for cleavage within the coding regions.

Creation and Use of Cassette Creation Vectors

In order to be useful in assembling DNA fragments, the gene fragments must be flanked by appropriately disposed cleavage sites. The skilled artisan will recognize that these sequences can be added in a number of ways, giving the same final product. For example, synthetic or naturally-occurring oligonucleotide duplexes containing correctly disposed nicking sites and associated sequences can be ligated to the ends of a desired fragment. Alternatively, PCR primers can be designed with priming sequences preceded by 5' tails containing correctly disposed nicking sites, thus adding the appropriate sequences during the PCR reaction. Site-directed mutagenesis can also be used to introduce sites in desired locations. Whatever the method of attaching appropriately disposed sites, the operation of the single-stranded regions is expected to be the same.

Figure 7:
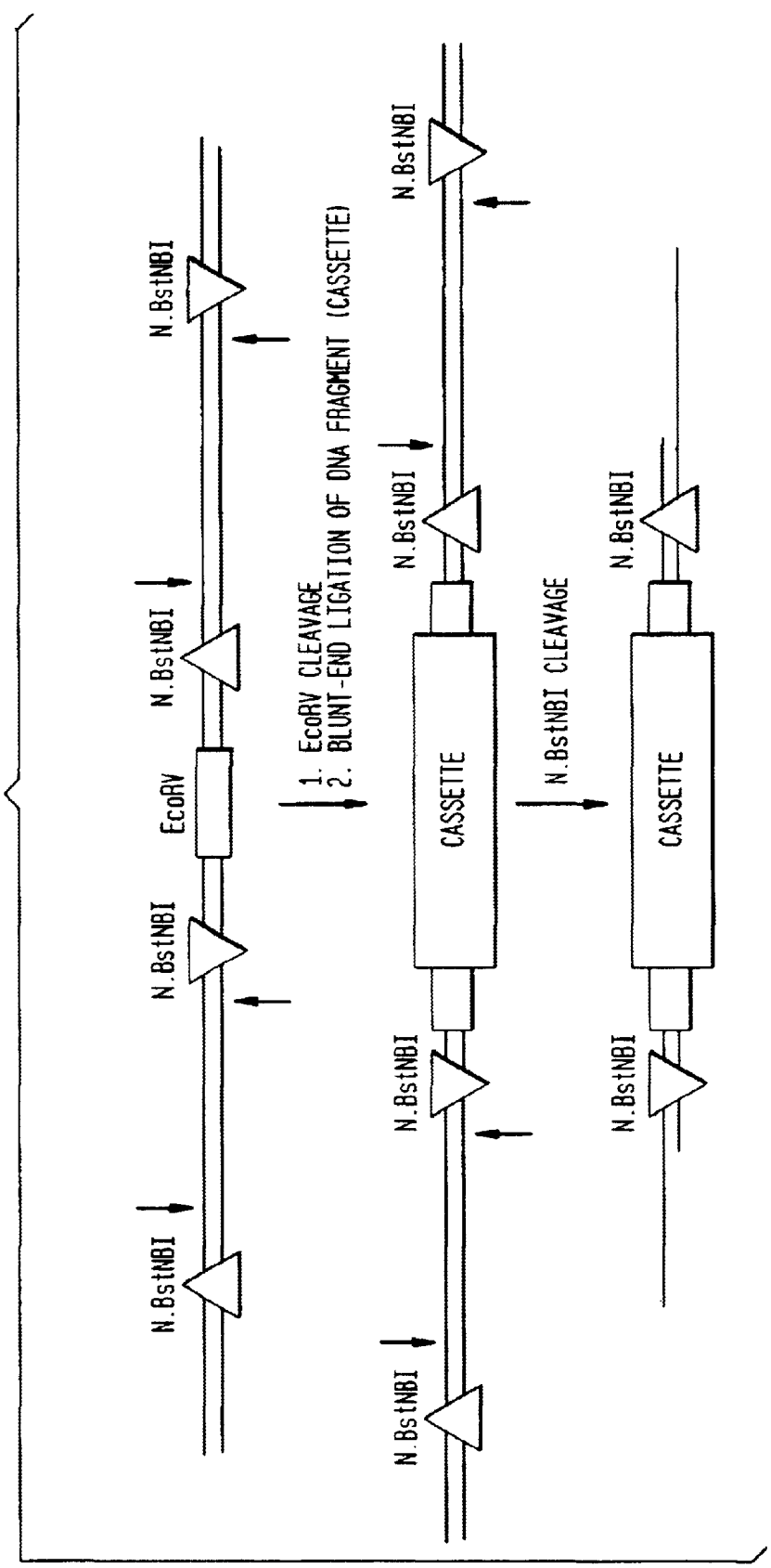
FIG. 7: Sample scheme to create a family of DNA fragments flanked by identical N.BstNBI 18-nucleotide cohesive ends.

Alternatively, the desired DNA fragment can be inserted between pre-existing flanking sequences. Successful insertion and growth of the plasmid allows cleavage and isolation of the fragment with appropriate single-stranded cohesive termini flanking the inserted fragment (FIG. 7). One utility of such a cassette creation vector is the ability to accumulate a family of DNA fragments, each bounded by identical cohesive termini. These could be useful as interchangeable parts, for example in an expression vector. Multiple families of such elements would allow rapid assembly of DNA arrays, for example containing a desired replication origin, a selective marker, promoters, enhancers and associated control elements, allowing constitutive and regulated gene expression, auxiliary factors (such as repressors and activators, and inhibitors), and a gene or DNA sequence of interest.

Use of Cohesive Ends Created by Site-Specific Nicking Enzymes

The creation of single-stranded regions can be useful in a variety of applications. First, and as documented in the examples, these regions can be used for oriented assembly of multiple DNA fragments, either into linear arrays or into circular molecules. Such concatenates are useful, for example, in assembly of cloning vectors, placing inserts into cloning vectors, assembling DNA fragments of discrete molecular weights to be used as molecular weight standards in DNA analysis, and in joining gene coding regions to transcriptional and translational control elements to allow expression of the gene coding region.

It is worth noting that the present invention provides methods for creating cohesive DNA termini of virtually any composition, and as such termini can be created to be complementary to cohesive ends created by restriction endonucleases. This provides a means for meshing this technology with pre-existing cloning systems that utilize cohesive ends. Fragments generated by the present invention can thus be joined to those created by restriction endonucleases, homing endonucleases or enzymes such as lambda int.

The ability to selectively expose single-stranded regions in duplex DNA is useful in a variety of applications. For example, exposing such regions allows selective mutagenesis of such exposed regions by single-strand specific mutagenesis such as bisulfite. Single-stranded gaps are also preferred over double-stranded regions as binding sites for oligonucleotides, such as those that might be employed for oligonucleotide-directed mutagenesis (Zoller and Smith, *DNA* 3:479–488 (1984)).

Single-stranded regions, whether internal gaps or terminal cohesive ends, can serve as annealing sites for probes, providing a means for sequence-specific detection of the exposed region, and in turn the attached DNA fragment. For example, DNA fragments could be encoded with unique sequence tags that could be revealed as single-strand regions using the present invention. DNA fragments bearing a given code can then be identified by annealing the code complement, bearing a detection reagent, to the family of DNA fragments. Only the desired DNA fragment will then be illuminated. Detection reagents might include radioactive, fluorescent, or antigenic moieties attached to or incorporated into the probe.

The single-strand regions exposed via the present invention can also be used in a purification scheme to isolate specific fragments of DNA. The DNA fragment containing the exposed single-stranded region is passed over a solid support to which has been affixed a single-stranded DNA containing a sequence complementary to that exposed region, or a portion thereof. The skilled artisan will recognize that there are conditions of salt, buffer and temperature at which only the complementary sequences will bind to the solid matrix, and those not binding can be washed off. Elution of the desired fragment can be accomplished by changing the binding conditions, for example by raising the binding temperature, preferably in a buffer of low ionic strength, to release the bound DNA.

The present invention is further illustrated by the following Examples. These Examples are provided to aid in the understanding of the invention and are not construed as a limitation thereof.

The references cited above and below are herein incorporated by reference.

EXAMPLES

While several of the following examples were established with the enzyme N.BstNBI, any sequence-specific nicking enzyme may be substituted in accordance with the present invention. The sequence listings in the below plasmids are most often inferred from the sequence of the original plasmids, and do not reflect possible errors introduced during construction, for example by replication errors during PCR.

Example 1

Generation of Three 18-Nucleotide Cohesive Sequences

To test the effectiveness of creating and using N.BstNBI-derived cohesive ends in cloning, three such termini were devised and created. A number of random sequences were generated that matched the criteria detailed above. To that end, the following steps were taken:

1) Generate a random 18-nucleotide sequence from a pool of four G, five A, five C and four T residues.

2) Use the GCG (Genetics Computer Group, Inc., Madison, Wis.) program foldRNA (Chan, et al., *Nucleic Acids Res.* 19:353–358 (1991)) to calculate the free energy for the most stable conformer of the single strand. Give preference to those with the most unfavorable folding energies.

3) Using the GCG program Mapsort (Genetics Computer Group, Inc., Madison, Wis.), check for the occurrence of restriction enzyme recognition sites (within the overlap and contiguous sequences), particularly for that of N.BstNBI or for those of enzymes with recognition sequences longer than four nucleotides. Give preference to those sequences lacking restriction sites, taking into account flanking contiguous sequences.

4) Using the GCG (Genetics Computer Group, Inc., Madison, Wis.) program GAP (Needleman and Wunsch, *J. Mol. Biol.* 48:443–453 (1970)), check for self-hybridization and for predicted hybridization between all possible sets of single-strand ends (the sequence itself and its complement). Note the number of Watson-Crick base pairs in the match, the number of consecutive base pairs, and the length of the gap between paired nucleotides. Also note whether the predicted pairing creates a nicked junction or a gap. Give preference to those with minimal predicted base pairing, and with gaps created in the most stable minimal base pairing scheme.

5) When restriction sites are apparent, or when particular base pairing interferes with desired patterns, swap nucleotides within the sequence and test again.

The cohesive ends generated in this example were selected from those best fitting the above criteria from a limited pool of randomly generated sequences. Table 1 lists 18 nucleotide sequences analyzed using this protocol, with the first sequence in each of the seven sets being the initially generated sequence, and subsequent entries being variants of that sequence designed to better conform to the established criteria. One column also reports the free energy calculated for the given sequence (The underlined sequences are those actually used in the later Examples).

TABLE 1

Generated 18 nucleotide regions, with predicted folding energy calculated by the GCG program fold RNA.

| | Sequence | energy |
|---|---|---|
| I. | GCGTCTAAACCCAGATGT | (aaa) -3.5 (SEQ ID NO:16) |
| | GCGTTCAAACCCAGATGT | (aab) -0.5 (SEQ ID NO:17) |

TABLE 1-continued

Generated 18 nucleotide regions, with predicted folding energy calculated by the GCG program fold RNA.

| | Sequence | | energy |
|---|---|---|---|
| II. | AGCTGTTCTAAGCCGCAA | (aac) | -0.8 (SEQ ID NO:18) |
| III. | TGTGAACACCTCGTAACG | (aad) | -0.6 (SEQ ID NO:19) |
| IV. | TTCCCAAGCACATGGGAT | (aae) | -5.6 (SEQ ID NO:20) |
| | TCTCCAAGCACAGTGAGT | (aaf) | 0.3 (SEQ ID NO:21) |
| V. | TGACTCAAGCGAGTACTC | (aag) | -0.2 (SEQ ID NO:22) |
| | TGACTCAAGCGGATACTC | (aah) | 1.5 (SEQ ID NO:23) |
| | <u>TGACCTAAGCGGATACTC</u> | (aaz) | 1.5 (SEQ ID NO:24) |

TABLE 1-continued

Generated 18 nucleotide regions, with predicted folding energy calculated by the GCG program fold RNA.

| | Sequence | | energy |
|---|---|---|---|
| VI. | ACTGAGCGCCATGCATTA | (aai) | -1.2 (SEQ ID NO:25) |
| | ACTGAGCGCCAGTCATTA | (aaj) | 1.0 (SEQ ID NO:26) |
| | ATCGAGCGCCATGCATTA | (aak) | 1.0 (SEQ ID NO:27) |
| | <u>ATCGAGCGCCTAGCATTA</u> | (aal) | 1.0 (SEQ ID NO:28) |
| VII. | <u>TGTACCATCGCTAACAGG</u> | (aay) | 0.4 (SEQ ID NO:29) |

TABLE 2

GCG GAP Analysis of test pairs

| | aaf | aaz | aal | aay |
|---|---|---|---|---|
| aaf | 18/18/0 | | | |
| rev | 8/3/0 | | | |
| aaz | 7/3/2 | 18/18/0 | | |
| rev | 6/2/1 | 6/2/3 | | |
| aal | 7/5/1 | 6/4/3 | 18/18/0 | |
| rev | 6/3/8 | 7/3/1 | 6/1/1 | |
| aay | 8/2/0 | 7/3/1 | 6/3/1 | 18/18/0 |
| rev | 7/3/0 | 6/4/1 | 6/3/6 | 6/2/0 |

The indicated oligonucleotides, as listed in Table 1, were processed pairwise using the GCG program GAP. Numbers record results derived from the program output. The first number is the total number of base pairs formed, the second number indicates the longest series of consecutive base pairs among those pairs, and the final number indicates the length of the gap predicted at the terminus. For example, the output of aaz paired with aal is:

```
1 TGACCTAAGCGGATACTC... 18   (aaz)  (SEQ ID NO:24)
          ||||  ||
1 ...ATCGAGCGCCTAGCATTA 18   (aal)  (SEQ ID NO:28)
``` displaying six base pairs, with four consecutive base pairs and a gap of three nucleotides at the terminus. Lines preceded by "rev" record values for the complement of the indicated sequence.

The three most favorable sequences among those tested were aaz, aal and aay. These were framed within N.BstNBI sites to create, after cleavage (indicated by ▽ or ▵), 18-nucleotide cohesive ends:

5' GAGTCTGAC▽ATCGAGCGCCTAGCATTA GTCAGACTC 3'  N1  (SEQ ID NO:30)

3' CTCAGACTG TAGCTCGCGGATCGTAAT▵CAGTCTGAG 5'  N1'

5' GAGTCCGAT▽TGACCTAAGCGGATACTC TGACGACTC 3'  N2  (SEQ ID NO:31)

3' CTCAGGCTA ACTGGATTCGCCTATGAG▵ACTGCTGAG 5'  N2'

5' GAGTCTCAG▽CCTGTTAGCGATGGTACA TGACGACTC 3'  N3  (SEQ ID NO:32)

3' CTCAGAGTC GGACAATCGCTACCATGT▵ACTGCTGAG 5'  N3'

As a naming convention, the 18-nucleotide cohesive ends were designated "N" with a number indicating a unique end. A prime symbol (') indicates the complementary strand.

Example 2

Creation of Vector Cassettes with Cohesive Termini

A plasmid was created that could generate individual origin and ampicillin resistance elements flanked by N.Bst-NBI elements disposed to create joinable 18-nucleotide cohesive ends. The plasmid was created by ligating together two PCR fragments, one containing the replication origin from pUC19, and the other containing the ampicillin resistance gene, again from pUC19. The primers used for PCR contained extra sequence elements, including appropriately disposed N.BstNBI recognition sites and sequences to create 18-nucleotide cohesive sequences fitting the criteria outlined above. All oligonucleotides used in this example and others described in the present invention were from New England Biolabs Organic Synthesis Division (Beverly, Mass.).

PCR was performed to generate fragments as follows:

Replication origin cassette: 1× NEB Thermopol buffer, 0.1 mg/ml bovine serum albumen, 0.4 mM dNTPs, 0.5 μM primer 216-112 (SEQ ID NO:4), 0.5 μM primer 216-117 (SEQ ID NO:3), 1 μg/ml pUC19 DNA (New England Biolabs, Beverly, Mass.), 4 mM $MgSO_4$ in a final volume of 0.5 ml. Five Units of Vent® DNA polymerase (New England Biolabs, Beverly, Mass.) were added, and the sample was then heated to 94° C. for 3 minutes, followed by 20 rounds of thermocycling: 94° C. (15 seconds), 58° C. (15 seconds), 72° C. (60 seconds). The sample was then phenol extracted and ethanol precipitated. The sample was suspended in gel-loading buffer and run on a 1% agarose gel in TBE. The correct size band was excised and eluted using an Elutrap® elution chamber (Schleicher & Schuell, Keene, N.H.) at 200 volts in 0.5× TBE for two hours. The eluted sample was collected, extracted with phenol and ethanol precipitated.

Ampicillin resistance cassette: 1× NEB Thermopol buffer, 0.1 mg/ml bovine serum albumen, 0.4 mM dNTPs, 0.5 µM primer 216-113 (SEQ ID NO:1), 0.5 µM primer 216-114 (SEQ ID NO:2), 1 µg/ml pUC19 DNA (New England Biolabs, Beverly, Mass.), 8 mM MgSO$_4$ in a final volume of 0.5 ml. Five Units of Vent® DNA polymerase (New England Biolabs, Beverly, Mass.) were added, and the sample was then heated to 94° C. for 3 minutes, followed by 20 rounds of thermocycling: 94° C. (15 seconds), 58° C. (15 seconds), 72° C. (60 seconds). The sample was then phenol extracted and ethanol precipitated. The sample was suspended in gel-loading buffer and run on a 1% agarose gel in TBE. The correct size band was excised and eluted using an Elutrap® elution chamber (Schleicher & Schuell, Keene, N.H.) at 200 volts in 0.5× TBE for two hours. The eluted sample was collected, extracted with phenol and ethanol precipitated.

Figure 4:
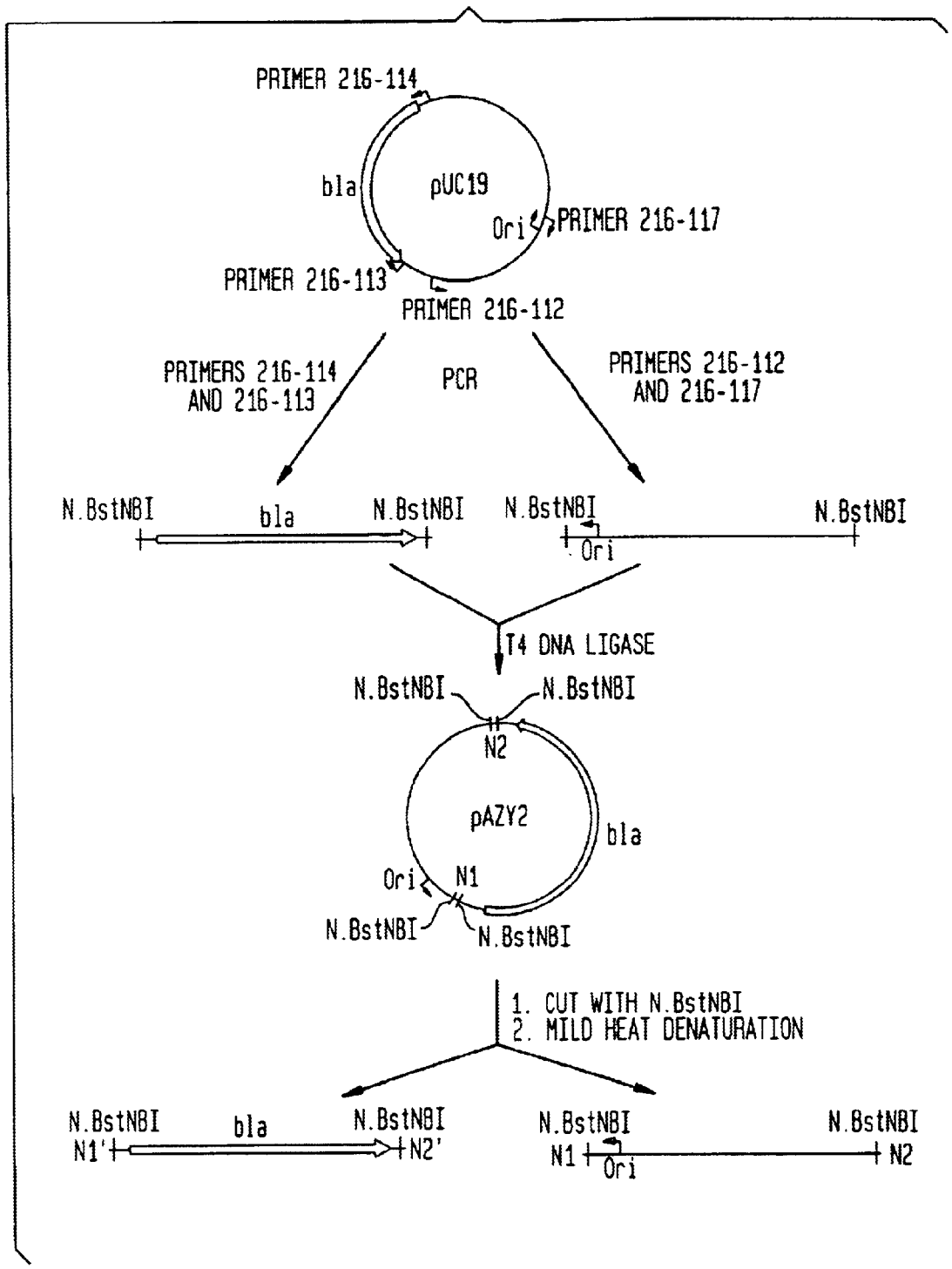
FIG. 4: Creating a vector (pAZY2) with two fragments, each flanked by N.BstNBI 18-nucleotide cohesive ends. bla=beta-lactamase gene. Ori=origin of replication.

The desired plasmid (FIG. 4) was created by ligating the above mentioned fragments, mixing approximately 10 ng of the replication origin PCR product with 30 ng of the ampicillin resistance PCR product in 1× NEBuffer T4 DNA ligase in a final volume of 20 µl. 400 Units of T4 DNA ligase (New England Biolabs, Beverly, Mass.) were added, and the reaction incubated at 16° C. overnight. Aliquots of the ligation reaction were transformed (The NEB Transcript 6:7 (1994)) into strain ER2502, and ampicillin-resistant colonies were screened for formation of a circular plasmid containing both elements oriented such that the direction of transcription for ampicillin resistance was the same as the direction of replication from the origin element. One such plasmid was pAZY2. This plasmid was transformed into strain ER2502, with transformants selected by growth on LB-ampicillin plates at 37° C. A single colony was used to inoculate 0.5 liter of LB (per liter, 10 g tryptone, 5 g yeast extract, 10 g NaCl, 1 g dextrose, 1 g MgSO$_4$·6H$_2$O, pH adjusted to 7.2 with NaOH) containing 0.1 mg/ml ampicillin, and the sample was grown overnight with shaking at 37° C. Plasmid DNA was isolated from the resulting culture with a Qiagen Mega-prep (Qiagen, Inc., Chatsworth, Calif.) as directed by the supplier. The concentration of the closed circular pAZY2 was determined by spectrophotometry.

The individual cassettes containing the origin of replication and ampicillin resistance elements were formed by cleavage of purified pAZY2 by N.BstNBI (New England Biolabs, Inc., Beverly, Mass.) using reaction conditions suggested by the supplier. Following cleavage by N.BstNBI, samples were heated to 75° C. for 20 minutes to dissociate the cohesive ends, and immediately loaded on a 1.4% agarose gel in 1× TBE buffer, where the fragments were separated by electrophoresis. The replication origin and ampicillin resistance cassettes were separately eluted in an Elutrap® elution chamber (Schleicher & Schuell, Keene, N.H.) for 2 hours in 0.5× TBE at 200 volts. Samples were phenol extracted, ethanol precipitated, dissolved in TE and quantified by running aliquots on a gel along with mass standards. The mass of DNA fragments was extrapolated by visual inspection.

Example 3

Vector Reassembly with Two DNA Fragments Containing 18-bp Cohesive Ends

The ability of the DNA fragments containing 18-bp cohesive termini to efficiently reassemble was tested by mixing together the separated ampicillin resistance and replication origin cassettes described in Example 2, and scoring reassembly by transformation. Assembly reactions contained 1× NEBuffer T4 DNA ligase and approximately 0.9 pM DNA (equivalent to 1 µg/ml of pAZY2). Samples contained either (1) covalently closed circular pAZY2, (2) the approximately 704 bp N.BstNBI fragment from pAZY2 containing the pUC19 origin of replication, (3) the approximately 1021 bp N.BstNBI fragment from pAZY2 containing the ampicillin resistance gene from pUC19, or (4) an equimolar mixture of the replication origin and ampicillin resistance gene fragments. 10 µl samples of each were incubated at room temperature for one hour alone or in the presence of 200 units of T4 DNA ligase (New England Biolabs, Beverly, Mass.).

After incubation, 1 µl of each assembly reaction was mixed with 50 µl of competent *Escherichia coli* cells (*The NEB Transcript* 6:7 (1994)) strain ER2502 on ice for 10 minutes. The samples were then placed in a 37° C. water bath for 45 seconds, and incubated on ice for 10 minutes. Cell samples were then diluted by addition of 1 ml of LB liquid media, and 0.1 ml of each diluted sample was plated onto LB agar plates containing 0.1 mg/ml ampicillin. Plates were incubated overnight at 37° C., and the number of colonies then determined.

TABLE 3

Transformation of a two-part re-assembly of pAZY2. The heading "ccc pAZY2" indicates covalently closed circular pAZY2; "ori" the N.BstNBI fragment derived from pAZY2 containing the pUC19 origin of replication; "amp$^R$" the N.BstNBI fragment derived from pAZY2 containing the pUC19 ampicillin resistance gene. Entries with numbers separated by a semi-colon are from replicate trials.

| ccc pAZY2 | ori | amp$^R$ | T4 DNA ligase | # colonies |
|---|---|---|---|---|
| + | | | + | 67 |
| + | | | | 93;128 |
| | + | | + | 0 |
| | + | | | 0;0 |
| | | + | + | 0 |
| | | + | | 0;0 |
| | + | + | + | 26 |
| | + | + | | 19;37 |

As seen in Table 3, no transformants were observed with the isolated origin of replication or ampicillin resistance DNA fragments alone. The number of colonies observed after assembly showed an efficient reassembly, with mixtures of the fragments yielding between 20–40% the number of colonies observed with the parent circular pAZY2 DNA. In these experiments, addition of T4 DNA ligase did not significantly change the number of transformants observed.

Example 4

Creation and Isolation of Cassettes Flanked by Cohesive Termini

For some applications it may be desirable to have a family of interchangeable DNA fragments, each flanked by a common set of cohesive termini. To facilitate the creation of such DNA fragments, a cloning vector was created in which a cloning site, in this case a unique EcoRV site, was situated between two pairs of correctly disposed N.BstNBI sites. After insertion of the DNA fragment of interest into the EcoRV site, in this example the ampicillin resistance gene, cleavage with N.BstNBI liberated this cloned gene cassette with 18-nucleotide cohesive termini.

Figure 5:
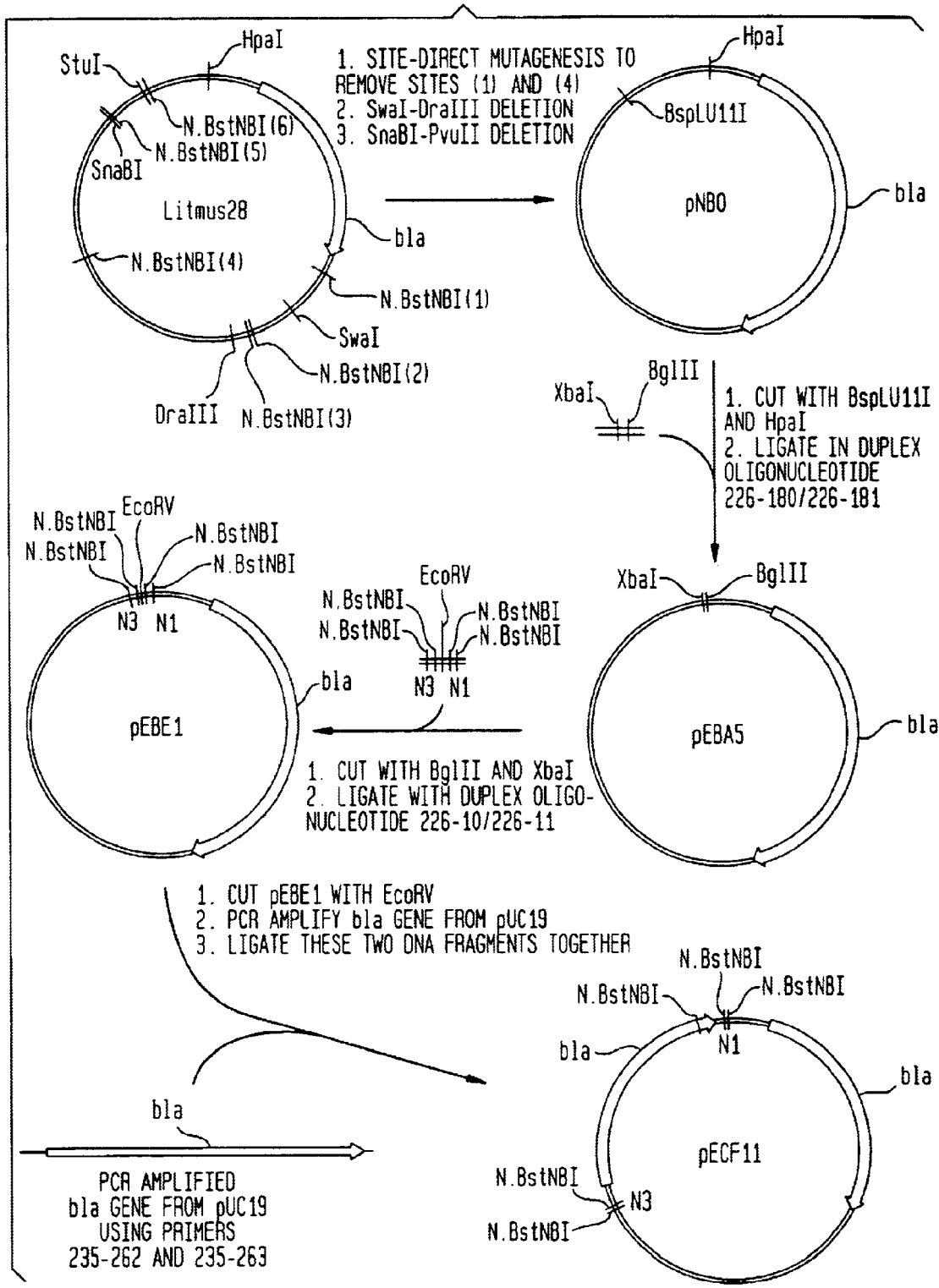
FIG. 5: Creating an ampicillin-resistance cassette flanked by N.BstNBI 18-nucleotide cohesive ends.
Figure 6:
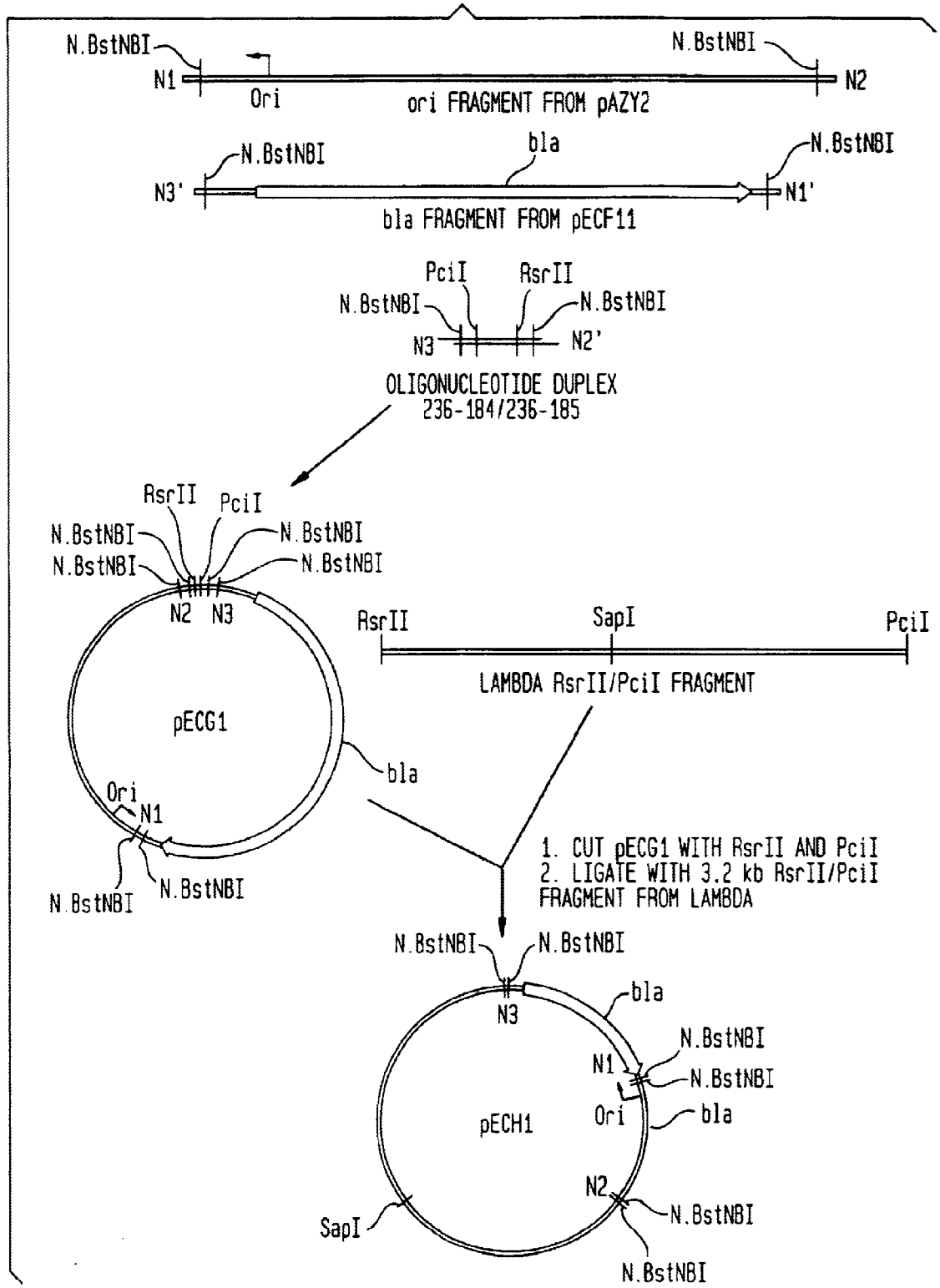
FIG. 6: Creating a plasmid (pECH1) from which three fragments can be generated by N.BstNBI cleavage, each resulting fragment flanked by 18-nucleotide cohesive ends.

The cloning vector in this example, pEBE1, was created via a multi-step assembly process (FIG. 5). The backbone for pEBE1 is the plasmid pNB0, a derivative of Litmus 28 (New England Biolabs, Beverly, Mass.) that contains no N.BstNBI sites and was created in the laboratory of Huimin Kong of New England Biolabs. Briefly, pNB0 was created using site-directed mutagenesis to alter the N-BstNBI sites within the beta-lactamase gene (coordinate 931) and replication origin region (coordinate 1939), while successive deletion of the SwaI/DraIII and SnaBI/PvuII fragments removed the remaining N.BstNBI sites. The pNB0 construct was cut with BspLU11I and HpaI and ligated to an oligonucleotide duplex of oligonucleotides 226-180 (SEQ ID NO:9) and 226-181 (SEQ ID NO:10), adding BglII and XbaI sites to the plasmid. The resulting plasmid was named pEBA5. The BglII/XbaI-cleaved pEBA5 was ligated to an oligonucleotide duplex (oligonucleotides 226-10/226-11; SEQ ID NO:7–8), adding two pairs of inwardly-directed N.BstNBI sites separated by an EcoRV site (vector pEBE1). This plasmid is thus configured to place a restriction fragment between two pairs of N.BstNBI sites, and upon treatment with N.BstNBI the liberated insert is flanked by unique 18-nucleotide cohesive ends, corresponding to N1 and N3 above.

An ampicillin resistance cassette was created by ligating a PCR product derived from pUC19 to pEBE1 cut with EcoRV. The PCR reactions were performed in 0.1 ml reaction mixtures containing 1× NEB Thermopol buffer, 0.1 mg/ml bovine serum albumen, 0.4 mM dNTPs, 1 µg/ml pUC19 DNA, 0.5 µM primer 235-262 (SEQ ID NO:11), 0.5 µM primer 235-263 (SEQ ID NO:12), 1 unit of Vent® DNA polymerase (New England Biolabs, Beverly, Mass.) and varying concentrations of $MgSO_4$ (4, 6, 8, 10 or 12 mM). PCR conditions were 94° C. for three minutes, then 20 cycles of 94° C. (15 seconds), 58° C. (15 seconds) and 72° C. (60 seconds). Following amplification, aliquots of each of the five reactions were run on an agarose gel and found to create an equivalent yield of the expected approximately 1 kb fragment. All samples were pooled, extracted with a phenol/chloroform mixture and ethanol precipitated. The precipitated sample was suspended in TE buffer (10 mM TrisHCl (pH 8.0), 1 mM EDTA), and subjected to agarose gel electrophoresis to further purify the product. The separated band was localized by UV fluorescence in the presence of ethidium bromide, and electroeluted at 200 volts for 2.5 hours in an Elutrap® apparatus using conditions specified by the manufacturer (Schleicher & Schuell, Keene, N.H.). The eluted sample was ethanol precipitated and suspended in TE buffer. This purified fragment was ligated to pEBE1 cut with EcoRV using standard conditions. One successful ligation product containing an ampicillin resistance gene transcribed in the same direction as plasmid replication was named pECF11. Cleavage of this construct with N.BstNBI, followed by heating at 65° C. for five minutes, liberated an ampicillin cassette flanked by 18-nucleotide cohesive ends.

Example 5

Construction of Plasmid Vector pECH1

A plasmid from which three fragments could be generated by N.BstNBI cleavage, each with two 18-nucleotide cohesive ends, was created by ligating a synthetic DNA duplex of oligonucleotides 236-184 (SEQ ID NO:13) and 236-185 (SEQ ID NO:14), with the replication origin N.BstNBI fragment isolated from pAZY2 and the ampicillin resistance N.BstNBI fragment from pECF11, the latter two fragments isolated as described above. The oligonucleotide duplex was annealed by mixing 1 µM of each single strand in 0.2 ml annealing buffer (20 mM TrisHCl (pH 7.6), 50 mM NaCl, 10 mM $MgCl_2$) in a 1.5 ml eppendorf tube. This mixture was floated in a 400 ml beaker filled with 95° C. water, and the beaker left out at room temperature until the temperature of the water was below 30° C. In this assembly, all three fragments have complementary 18-nucleotide cohesive ends, permitting a unique, oriented assembly of the fragments.

The assembly was accomplished by incubating approximately 4 ng of the origin-containing fragment, 6 ng of the ampicillin resistance-containing fragment, and 0.3 ng of the oligonucleotide duplex in 10 µl of NEBuffer T4 DNA ligase at room temperature for 1 hour. Following this incubation, 2 µl of the assembly mixture was transformed into ER2502 as described above, and transformants selected by growth on LB-ampicillin plates at 37° C. One desired construct was named pECG1. pECG1 was further modified by cutting with RsrII (New England Biolabs, Beverly, Mass.) and PciI (SibEnzymes, Novosibirsk, Russia), and ligating this vector to an approximately 3.2 kb DNA fragment isolated from lambda DNA after cleavage with RsrII and PciI. The resulting construct was named pECH1. Digestion with N.BstNBI resulted in three DNA fragments, approximately 3.2, 1.0 and 0.7 kb in length.

Example 6

Vector Reassembly with Three DNA Fragments Containing 18-Nucleotide Cohesive Termini Vector assembly was repeated, similar to that described in Example 3, but using three fragments produced by N.BstNBI cleavage (Example 4) of pECH1. Cleavage of pECH1 by N.BstNBI resulted in the three fragments described in Example 5. The digested N.BstNBI fragments were drop-dialyzed on 0.025 µM nitrocellulose filters (Millipore Corporation, Bedford, Mass.) against TE, then heated to 65° C. for 3 minutes. Fragments were then separated by electrophoresis on a 1% agarose gel in 0.5× TBE, with both the gel and buffer pre-heated to 65° C. The fragments were excised and eluted using an Elutrap® elution chamber (Schleicher & Schuell, Keene, N.H.) at 200 volts in 0.5× TBE for 3 hours. The eluted samples were collected, extracted with phenol and ethanol precipitated. Finally, the samples were suspended in TE buffer and quantified by visual inspection after running aliquots alongside DNA mass standards on an agarose gel.

In this case, DNA assembly was performed at a concentration of about 0.3 nM of each fragment, corresponding to about 1 µg/ml of pECH1. Assembly was performed in NEBuffer N.BstNBI (10 mM TrisHCl (pH 7.5 at 25° C.), 10 mM $MgCl_2$, 0.15 M KCl, 1 mM dithiothreitol) at room temperature for 1 hour. From the assembly reactions, 1 µl aliquots were transformed into 50 µl aliquots of ER2502 using standard protocols, and diluted into 1 ml LB broth. Samples (0.3 ml) of the diluted transformants were plated on LB-ampicillin plates and grown overnight at 37° C. No transformants were observed in assembly reactions containing a single DNA fragment, or any two of the fragments. When all three fragments were present, 16 colonies were observed, compared with 126 colonies obtained with the covalently closed circular pECH1 DNA. This corresponds to a transformation efficiency of $5.3 \times 10^4$ cfu/ug for the assembled pECH1 and $4.2 \times 10^5$ cfu/ug of covalently closed circular pECH1.

Figure 8:
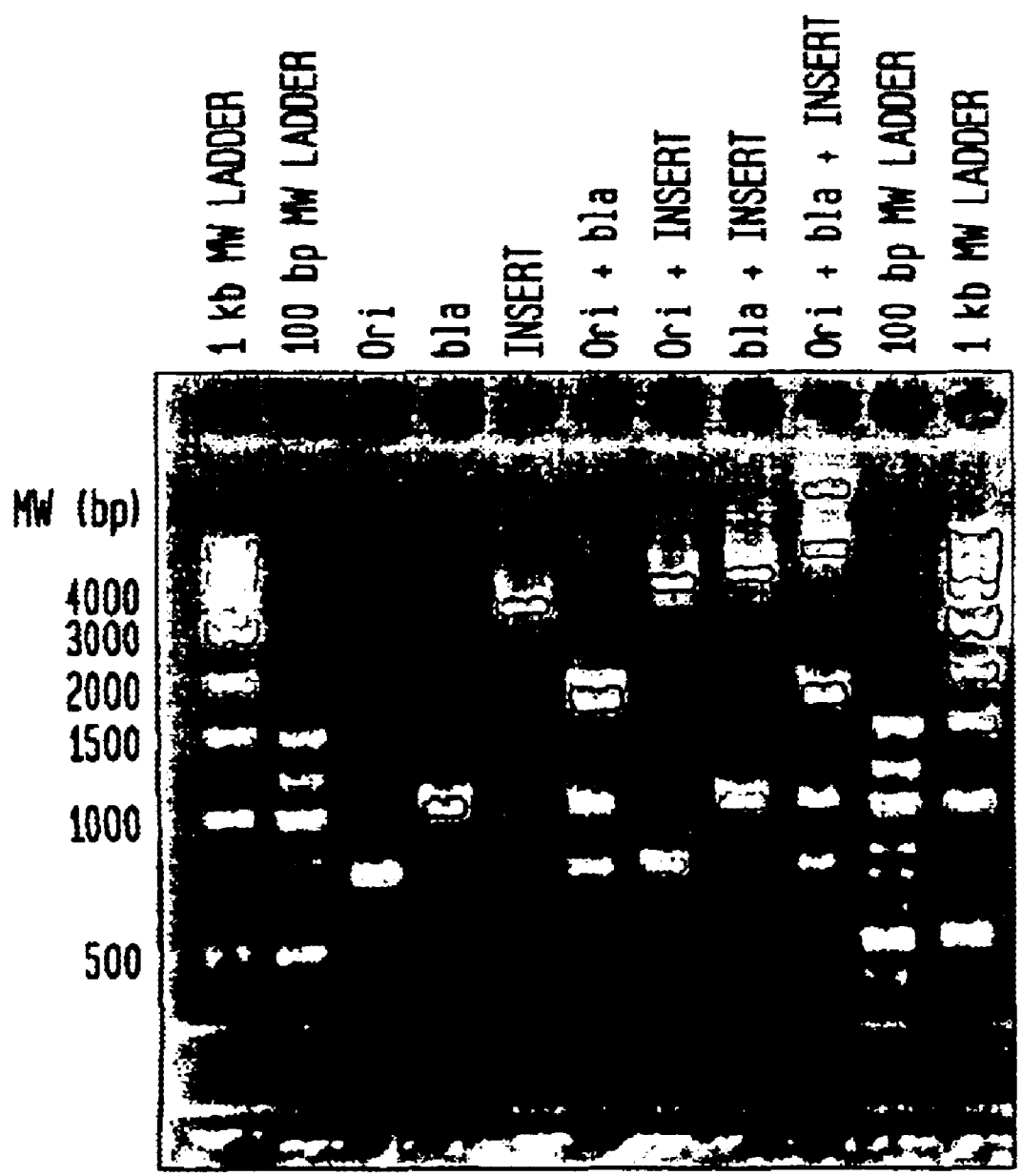
FIG. 8: Agarose gel analysis of assembly of three fragments with 18-nucleotide cohesive ends.

Reassembly was also visualized by mixing these three fragments and observing the assembled products by gel electrophoresis. Arrays containing 15 ng of each fragment in 10 µl of 1× NEBuffer N.BstNBI were mixed, and incubated at room temperature for 30 minutes, then separated by electrophoresis on a 1% agarose gel in 1× TBE buffer along with MW standards from New England Biolabs (FIG. 8). The individual fragments ran as single bands, while pairwise combinations yielded an additional band of the expected molecular weight. Combinations with the larger fragment (3.2 kb) were largely depleted for this fragment, as would be expected since its molar concentration was 3–4-fold lower than the origin of replication or ampicillin resistance fragment. Mixing the origin of replication and ampicillin resistance fragments led to formation of the expected hybrid, although not all fragments were assembled. Finally, mixtures of all three fragments gave a series of higher molecular weight species, presumably reflecting linear, relaxed open circular molecules, or concatamers thereof.

Example 7

Vector Reassembly with Four DNA Fragments

The plasmid pECH1 was also used as a source of DNA fragments to evaluate a four-part assembly of fragments, in this case where one of the joining junctures is the three-nucleotide overhang generated by SapI. The 3.2 kb N.Bst-NBI fragment from pECH1 was cut with SapI, yielding two fragments of approximately 1.4 and 1.8 kb. Assembly reactions of 20 µl contained 1× NEBuffer N.BstNBI with approximately 2 nM of four DNA fragments derived from pECH1, namely the three fragments described in Example 6, with the 3.2 kb fragment additionally cut by SapI. After incubation at room temperature for 1 hour, the volume of the reaction was increased to 30 µl by addition of ATP (final concentration 0.67 mM) and T4 DNA ligase (final concentration 13 U/µl; New England Biolabs, Beverly, Mass.). After mixing, this sample was incubated at 16° C. for 2 hours. Aliquots of this ligated mixture were transformed into 50 µl aliquots of competent ER2502 cells, which were in turn plated on LB-ampicillin media and incubated overnight at 37° C. to select for transformants. Equivalent quantities of covalently closed circular pECH1 were transformed in parallel.

TABLE 4

Transformation of a four-part reassembly of pECH1. The heading "Closed circular" represents uncleaved covalently closed circular pECH1; "Reassembled" represents the assembly of the four fragments derived from pECH1 by cleavage with N.BstNBI and SapI, as described in Example 7. Colony forming units = cfu.

|  | Closed Circular | Reassembled |
|---|---|---|
| Trial 1 | $9.4 \times 10^5$ cfu/µg | $9.1 \times 10^5$ cfu/µg |
| Trial 2 | $2.1 \times 10^5$ cfu/µg | $9.6 \times 10^4$ cfu/µg |
| Trial 3 | $2.5 \times 10^5$ cfu/µg | $1.8 \times 10^5$ cfu/µg |

Example 8

Generation of 12-Bp Cohesive End Sequences

In theory, the length of the cohesive ends could be nearly any value. At the two extremes, too short a region limits the base pairing and stacking interactions that support duplex formation, and joining is not stable. On the other hand, too large a region leaves the cleaved ends so stable that separation and purification of the DNA fragments is difficult. The examples above have used 18-nucleotide cohesive ends. For comparison, and to demonstrate the universality of the approach, ligation assemblies were also performed with 12-nucleotide cohesive ends, again generated by N.BstNBI.

The methodology of Example 1 was used to generate 12-nucleotide cohesive ends. Procedures were the same, except the randomized sequence was 12 nucleotides in length rather than 18. Table 5 lists 12 randomly generated sequences along with their predicted RNA folding energies. Table 6 takes a subset of these sequences and compares predicted, most stable pairing configurations for a subset of these sequences.

TABLE 5

Generated 12 nucleotide regions, with predicted folding energy calculated by the GCG program fold RNA.

| Sequence |  |  | foldRNA energy |
|---|---|---|---|
| GTAGTTACGCCA | (baa) | (SEQ ID:35) | 2.4 |
| CAATGTTGCGAG | (bab) | (SEQ ID:36) | 4.1 |
| TCTCAATGAGGC | (bac) | (SEQ ID:37) | 1.4 |
| AGCGAGCCTTTA | (bad) | (SEQ ID:38) | 2.7 |
| TGATCGAGACCT | (bae) | (SEQ ID:39) | 5.9 |
| TCTGCGGATAAC | (baf) | (SEQ ID:40) | 3.6 |
| TATGCAGCGCAT | (bag) | (SEQ ID:41) | 1.3 |
| GATCGAACGTTC | (bah) | (SEQ ID:42) | 1.8 |
| AAATTTGGGCCC | (bai) | (SEQ ID:43) | 2.0 |
| ACTATCTGGAGC | (baj) | (SEQ ID:44) | 2.6 |
| AGGCGACATTTC | (bak) | (SEQ ID:45) | 2.8 |
| ATTTACGGGCCA | (bal) | (SEQ ID:46) | 5.9 |

TABLE 6

GCG GAP Analysis of test pairs, 12-nucleotide. The indicated oligonucleotides, as listed in Table 5, were processed pairwise using the GCG program GAP. Numbers record results derived from the program output. The first number is the total number of base pairs formed, the second number indicates the longest series of consecutive base pairs among those pairs, and the final number indicates the length of the gap predicted at the terminus.

|  | baa | bab | bad | bae | baf | baj | bak | bal |
|---|---|---|---|---|---|---|---|---|
| baa | 12/12/0 |  |  |  |  |  |  |  |
| . . . rev | 6/2/1 |  |  |  |  |  |  |  |
| bab | 6/4/1 | 12/12/0 |  |  |  |  |  |  |
| . . . rev | 4/2/0 | 6/3/4 |  |  |  |  |  |  |
| bad | 4/2/2 | 4/3/2 | 12/12/0 |  |  |  |  |  |
| . . . rev | 5/3/1 | 5/2/1 | 4/2/1 |  |  |  |  |  |

TABLE 6-continued

GCG GAP Analysis of test pairs, 12-nucleotide. The indicated oligonucleotides, as listed in Table 5, were processed pairwise using the GCG program GAP. Numbers record results derived from the program output. The first number is the total number of base pairs formed, the second number indicates the longest series of consecutive base pairs among those pairs, and the final number indicates the length of the gap predicted at the terminus.

|  | baa | bab | bad | bae | baf | baj | bak | bal |
|---|---|---|---|---|---|---|---|---|
| bae | 4/2/0 | 4/2/0 | 7/4/2 | 12/12/0 | | | | |
| . . . rev | 4/2/1 | 5/2/2 | 5/2/0 | 6/2/0 | | | | |
| baf | 4/2/3 | 4/2/1 | 4/2/2 | 4/2/1 | 12/12/0 | | | |
| . . . rev | 5/4/3 | 5/3/1 | 4/2/1 | 5/3/1 | 6/2/2 | | | |
| baj | 4/1/2 | 5/2/1 | 4/4/5 | 6/3/1 | 5/3/2 | 12/12/0 | | |
| . . . rev | 4/3/6 | 4/2/1 | 4/2/1 | 6/3/1 | 7/4/0 | 4/2/0 | | |
| bak | 4/2/4 | 5/2/3 | 6/3/6 | 5/3/1 | 4/2/2 | 3/2/6 | 12/12/0 | |
| . . . rev | 7/4/0 | 8/5/1 | 5/4/3 | 5/3/6 | 3/2/4 | 5/2/2 | 6/2/4 | |
| bal | 6/4/2 | 4/2/3 | 5/3/3 | 5/2/1 | 6/3/1 | 5/2/0 | 3/1/2 | 12/12/0 |
| . . . rev | 4/2/2 | 5/3/3 | 5/2/2 | 5/2/0 | 5/2/0 | 4/3/6 | 4/1/1 | 4/1/1 |

The three most favorable sequences among those tested were bab (SEQ ID NO:36), bal (SEQ ID NO:46) and baj (SEQ ID NO:44). These were framed within N.BstNBI sites to create, after cleavage (indicated by $^\nabla$ or $_\Delta$), 12-nucleotide cohesive ends:

```
5'GAGTCAGCT▽CAATGTTGCCAG TCAGGACTC 3'    M1   (SEQ ID NO:47)

3'CTCAGTCGA GTTACAACGGTC△AGTCCTGAG 5'    M1'

5'GAGTCCGAT▽ATTTACGGGCCA CGTAGACTC 3'    M2   (SEQ ID NO:48)

3'CTCAGGCTA TAAATGCCCGGT△GCATCTGAG 5'    M2'

5'GAGTCTCAG▽ACTATCTGGAGC GACTGACTC 3'    M3   (SEQ ID NO:49)

3'CTCAGAGTC TGATAGACCTCG△CTGACTGAG 5'    M3'
```

As a naming convention, the 12-nucleotide cohesive ends were designated "M" with a number indicating a unique end. A prime symbol (') indicates the complementary strand.

Example 9

Creation of Vector Cassettes with 12-Nucleotide Cohesive Termini

A plasmid was created that could generate the individual origin and ampicillin resistance elements flanked by N.BstNBI elements disposed to create joinable 12-nucleotide cohesive ends. The end result, pECU7 (FIG. 9), is analogous to pECG1, differing primarily in the length of cohesive termini created by N.BstNBI cleavage. As a starting point in the construction, a plasmid was created by ligating together two PCR fragments, one containing the replication origin from pUC19, and the other containing the ampicillin resistance gene, again from pUC19. The primers used for PCR contained extra sequence elements including appropriately disposed N.BstNBI recognition sites and sequences to create 12-nucleotide cohesive termini fitting the criteria outlined above, and allowing unique, oriented reassembly.

PCR was performed to generate fragments as follows:

Replication origin cassette: 1× NEB Thermopol buffer, 0.1 mg/ml bovine serum albumen, 0.4 mM dNTPs, 0.5 µM primer 242-11 (SEQ ID NO:33), 0.5 µM primer 242-12 (SEQ ID NO:34), 0.1 µg/ml pUC19 DNA (New England Biolabs, Beverly, Mass.), 4 mM MgSO₄ in a final volume of 0.1 ml. One unit of Vent® DNA polymerase (New England Biolabs, Beverly, Mass.) was added, and the sample was then heated to 94° C. for 4 minutes, followed by 20 rounds of thermocycling: 94° C. (15 seconds), 58° C. (15 seconds), 72° C. (60 seconds). The sample was then phenol extracted and ethanol precipitated. The sample was suspended in gel-loading buffer and run on a 1% agarose gel in TBE buffer. The correct size band was excised and eluted using an Elutrap® elution chamber (Schleicher & Schuell, Keene, N.H.) at 200 volts in 0.5× TBE for 1.3 hours. The eluted sample was collected, extracted with phenol and ethanol precipitated. Finally, the sample was suspended in TE buffer.

Ampicillin resistance cassette: Reaction mixtures contained 1× NEB Thermopol buffer, 0.1 mg/ml bovine serum albumen, 0.4 mM dNTPs, 0.5 µM primer 222-14 (SEQ ID NO:5), 0.5 µM primer 241-83 (SEQ ID NO:6), 1 µg/ml pUC19 DNA (New England Biolabs, Beverly, Mass.) and either 0, 2, 4, 6 or 8 mM added MgSO₄, each in a final volume of 0.1 ml. One Unit of Vent® DNA polymerase (New England Biolabs, Beverly, Mass.) was added to each, and the samples were then heated to 94° C. for 3 minutes, followed by 20 rounds of thermocycling: 94° C. (15 seconds), 58° C. (15 seconds), 72° C. (60 seconds). Aliquots of the separate reactions were run on an agarose gel to assess the reaction products. The most complete products, from samples containing 2, 4, 6 or 8 mM added MgSO₄, were pooled, and purified by gel electrophoresis on a 1.4% agarose gel run in TBE buffer. The correct-sized band was excised and eluted using an Elutrap® elution chamber (Schleicher & Schuell, Keene, N.H.) at 200 volts in 0.5× TBE for 1.5 hours. The eluted sample was collected, extracted with phenol, ethanol precipitated and suspended in TE buffer. Approximately 2 µg of the purified fragment in a volume of 9 µl was mixed with 1 µl of 10× NEBuffer for T4 DNA ligase, and phosphorylated by addition of 5 units of polynucleotide kinase (New England Biolabs, Beverly, Mass.) and incubated at 37° C. for 45 minutes.

Figure 9:
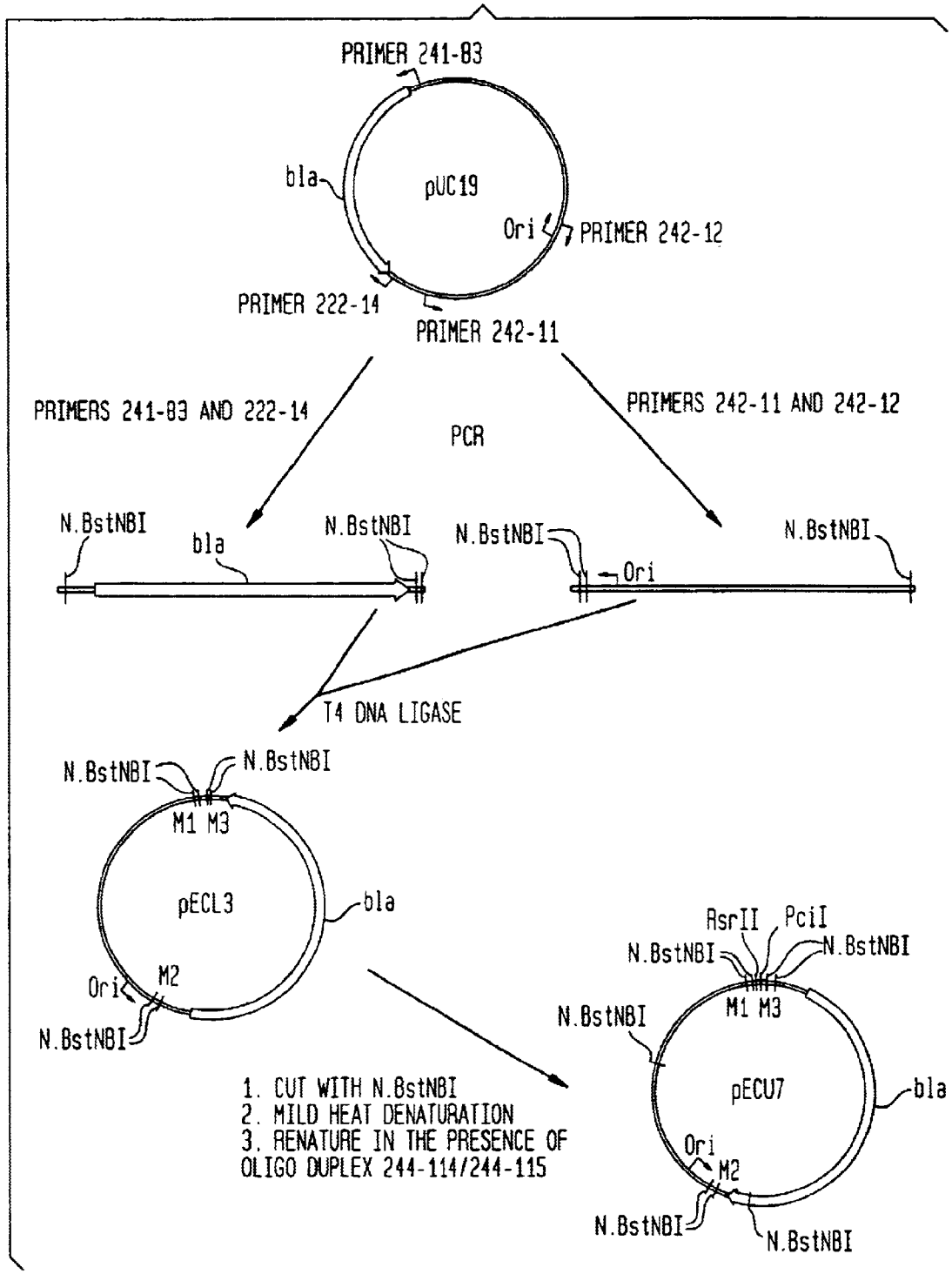
FIG. 9: Creating a plasmid (pECU7) from which three fragments can be generated by N.BstNBI cleavage, each resulting fragment flanked by 12-nucleotide cohesive ends.

The desired plasmid was created by ligating the above mentioned fragments, mixing approximately 0.1 μg of the replication origin PCR product with 0.3 μg of the ampicillin resistance PCR product in 1× NEBuffer T4 DNA ligase in a final volume of 20 μl. 2000 Units of T4 DNA ligase (New England Biolabs, Beverly, Mass.) were added, and the reaction incubated at 16° C. overnight. Aliquots of the ligation reaction were transformed (*The NEB Transcript* 6:7 (1994)) into strain ER2502, and ampicillin-resistant colonies were screened for formation of a circular plasmid containing both elements oriented such that the direction of transcription for ampicillin resistance was the same as the direction of replication from the origin element. One such plasmid was pECL3 (FIG. 9). This plasmid was transformed into strain ER2502, with transformants selected by growth on LB-ampicillin plates at 37° C. A single colony was used to inoculate 0.5 liter of LB containing 0.1 mg/ml ampicillin, and the sample grown overnight with shaking at 37° C. Plasmid DNA was isolated from the resulting culture with a Qiagen Mega-prep (Qiagen, Inc., Chatsworth, Calif.) as directed by the supplier. The concentration of pECL3 was determined by visually comparing UV fluorescence of aliquots of the samples relative to DNA mass standards run on an agarose gel.

The plasmid pECL3 was modified to add RsrII and PciI restriction sites between the adjacent N.BstNBI sites, allowing insertion of a "stuffer fragment." The plasmid pECL3 was digested with N.BstNBI, and approximately 25 ng of the digested plasmid was mixed with approximately 0.75 pmole of the DNA duplex prepared by annealing oligonucleotides 244-114 (SEQ ID NO:50) and 244-115 (SEQ ID NO:51; annealed as described in Example 5) and 2.5 μl of 10× NEBuffer T4 DNA ligase in a final volume of 25 μl. This sample was placed in a 70° C. water bath for five minutes to separate the 12-nucleotide cohesive ends in pECL3, then cooled at room temperature for 35 minutes. The oligonucleotide duplex was constructed to contain complementary cohesive ends that annealed to cohesive termini on the ampicillin and replication origin fragments created by N.BstNBI cleavage and selective denaturation of pECL3, and thus the reannealing generated a population of clones that contained the substituted oligonucleotide duplex. One such construct was named pECU7 (FIG. 9).

An approximately 3.2 kb fragment, derived via RsrII and PciI cleavage of lambda DNA (see Example 5), was ligated to pECU7 cleaved with the same two restriction endonucleases, yielding a construct pECV1, similar to pECH1.

Example 10

Vector Reassembly with Three DNA Fragments Containing 12-Nucleotide Cohesive Ends Vector assembly was repeated, similar to that described in Example 6, but using three fragments produced by N.BstNBI cleavage of pECV1 (see Example 9). Vector pECV1 was digested with N.BstNBI, followed by drop dialysis of the fragments on a 0.025 μM nitrocellulose filter (Millipore Corporation, Bedford, Mass.) against TE buffer. NaCl was added to bring the salt concentration to 30 mM, and the digested DNA was heated to 65° C. for 5 minutes before electrophoresis on a 1% agarose gel in 0.5× TBE. Both the gel and buffer were pre-heated to 62° C. The three fragments, approximately 3.2, 1.0 and 0.7 kb, were excised from the gel and eluted in an Elutrap® elution chamber (Schleicher & Schuell, Keene, N.H.) for 3 hours in 0.5× TBE at 200 volts. Samples were ethanol precipitated, dissolved in TE and quantified by agarose gel electrophoresis alongside DNA mass standards.

In this case, DNA assembly was performed at a concentration of about 3 nM each fragment, corresponding to 10 μg/ml of pECV1. Assembly was performed in TE augmented with 0.15 M KCl at room temperature for 1 hour. From the assembly reactions, 1, 3 or 5 μl aliquots (corresponding to about 10, 30 or 50 ng DNA) were transformed into 50 μl aliquots of ER2502 using standard protocols (*The NEB Transcript* 6:7 (1994)), and diluted to 0.2 ml with LB broth; the diluted transformation mixtures were plated on LB-ampicillin plates and incubated over the weekend at room temperature. As a control, about 5 ng of covalently closed circular pECV1 was transformed into 50 μl ER2502 cells and afterward, the transformation mixture was diluted to 1.0 ml with LB broth. Aliquots (20, 60 and 100 μl) of the diluted transformants were plated on LB-ampicillin plates and grown over the weekend at room temperature. No transformants were observed in assembly reactions containing a single DNA fragment, or any two of the fragments. When all three fragments were present, an average of $3.5 \times 10^3$ cfu/pg was observed, as compared with $3.4 \times 10^5$ cfu/pg in the control covalently closed circular pECV1.

Figure 10:
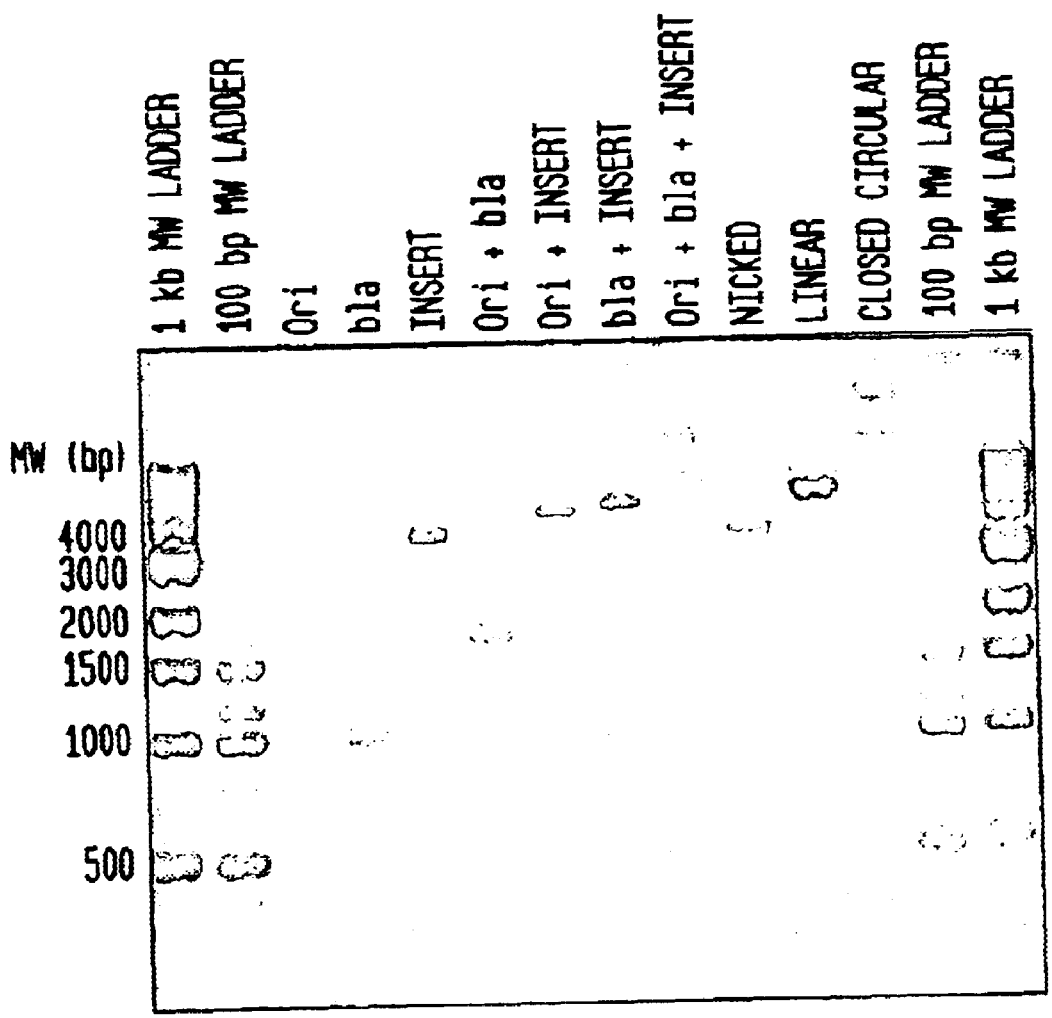
FIG. 10: Agarose gel analysis of assembly of three fragments with 12-nucleotide cohesive ends.

Reassembly was also visualized by mixing these three fragments, and observing the assembled products by gel electrophoresis. Arrays containing about 15–25 ng of each fragment in 10 μl of 1× NEBuffer N.BstNBI were mixed, and incubated at room temperature for 60 minutes, then separated by electrophoresis on a 1% agarose gel in 1× TBE buffer along with MW standards from New England Biolabs (FIG. 10). The individual fragments ran as single bands, while pairwise combinations yielded an additional band of the expected molecular weight, although not all fragments were assembled. Mixtures of all three fragments gave a series of higher molecular weight species, presumably reflecting linear, relaxed open circular molecules, or concatamers thereof.

Example 11

Vector Reassembly with Four DNA Fragments

Plasmid pECV1 was also used to generate DNA fragments for reassembly tests using four fragments. Similar to Example 7, this assembly included three N.BstNBI junctions (with 12-nucleotide overhangs) plus one SapI junction consisting of three-nucleotide overhangs. The SapI junction was derived from cleavage of the 3.2 kb N.BstNBI fragment from pECV1 with SapI, a process that yielded two fragments of approximately 1.4 and 1.8 kb. Assembly reactions of 8.7 μl contained 0.12 M KCl with approximately 1.5 nM of four DNA fragments derived from pECV1, namely the three fragments described in Example 10, with the 3.2 kb fragment additionally cut by SapI. After incubation at room temperature for 1 hour, the volume of the reaction was increased to 20 μl by the addition of ATP (final concentration 1 mM), MgCl$_2$, (final concentration 10 mM), DTT (final concentration 10 mM) and T4 DNA ligase (final concentration 20 U/μl; New England Biolabs, Beverly, Mass.). After mixing gently, this reaction mixture was incubated at 16° C. for 2 hours. Aliquots (2, 6 and 10 μl) of the ligation mixture, corresponding to about 10, 30 and 50 ng of DNA, were transformed into 50 μl ER2502 cells; LB media was added to the transformation mixtures, to a final volume of 0.2 ml and the transformants were plated on LB-ampicillin media and incubated overnight at 37° C. As a control, 5 ng of covalently closed circular pECV1 was transformed into 50 μl of ER2502 cells; the transformation mixture was diluted to 1.0 ml with LB broth and aliquots of 20 μl (about 0.1 ng), 60 μl (about 0.3 ng) or 100 μl (about 0.5 ng) were plated on LB-ampicillin plates which were then incubated overnight at 37° C. An average of $9.7 \times 10^3$ cfu/pg were seen in the 4-way reassembled pECV transformations compared with $1.5 \times 10^5$ cfu/pg of covalently closed circular pECV1.

What is claimed is:

1. A method for creating target single strand regions in a plurality of double stranded DNA molecules for use in joining the DNA molecules, comprising:

(a) nicking at least two sites bordering a target region within the DNA molecules with at least one site-specific nicking endonuclease;

(b) subjecting the nicked DNA molecules from step (a) to conditions that selectively denature the target region to create the target single stranded region; and (c) joining the DNA molecules from step (b) by means of the target single strand regions.

2. A method of claim 1 wherein the at least two sites bordering the target region are located on a single strand of the double stranded DNA so that the target single stranded region comprises a gap in the double stranded DNA.

3. A method for creating a target single strand region at a terminus of a linear double stranded DNA molecule for use in joining the DNA molecule to a second DNA molecule by means of the single strand region, or for detecting, purifying or selectively mutagenizing the DNA molecule, comprising (a) nicking at least one site bordering the target region at the terminus of the linear double stranded DNA with at least one site-specific nicking endonuclease;

(b) subjecting the nicked DNA molecules from step (a) to conditions that selectively denature the target region to create the target single stranded region; and (c) joining the DNA molecule to a second DNA molecule by means of the single strand region, or detecting, purifying or selectively mutagenizing the DNA molecule by means of the single strand region.

4. The method of claim 3 wherein the DNA terminus is pre-existing.

5. The method of claim 3 wherein the DNA terminus is formed by site-specific endonuclease cleavage.

6. A method for creating target single strand regions in a double stranded DNA molecule for use in detecting, purifying or selectively mutagenizing the DNA molecule, the method comprising:

(a) nicking at least two sites bordering a target region in the DNA molecule with at least one site-specific nicking endonuclease; and (b) subjecting the nicked DNA molecules from step (a) to conditions that selectively denature the target region for creating the target single stranded region; and
(c) detecting, purifying or selectively mutagenizing the DNA molecule by means of the target single strand region.

7. A method of claim 6, wherein the two sites bordering the target region are both located on a single strand of the double stranded DNA so that the target single stranded region comprises a gap in the double stranded DNA.

* * * * *

SEQUENCE LISTING

<160> NUMBER OF SEQ ID NOS: 51

<210> SEQ ID NO 1
<211> LENGTH: 40
<212> TYPE: DNA
<213> ORGANISM: Unknown
<220> FEATURE:
<223> OTHER INFORMATION: Description of Unknown Organism: Synthetic oligonucleotide

<400> SEQUENCE: 1
aaatcaatct aaagtatata ccggtaaact tggtctgaca                40

<210> SEQ ID NO 2
<211> LENGTH: 38
<212> TYPE: DNA
<213> ORGANISM: Unknown
<220> FEATURE:
<223> OTHER INFORMATION: Description of Unknown Organism: Synthetic oligonucleotide

<400> SEQUENCE: 2
ctagcattag tcagactcta cattcaaata tgtatccg                  38

<210> SEQ ID NO 3
<211> LENGTH: 38
<212> TYPE: DNA
<213> ORGANISM: Unknown
<220> FEATURE:
<223> OTHER INFORMATION: Description of Unknown Organism: Synthetic oligonucleotide

<400> SEQUENCE: 3
gcgctcgatg tcagactcga gcaaaaggcc agcaaaag                  38

<210> SEQ ID NO 4
<211> LENGTH: 56
<212> TYPE: DNA
<213> ORGANISM: Unknown
<220> FEATURE:
<223> OTHER INFORMATION: Description of Unknown Organism: Synthetic oligonucleotide

<400> SEQUENCE: 4
gagtccgatt gacctaagcg gatactctga cgactcgtag aaaagatcaa aggatc    56

<210> SEQ ID NO 5
<211> LENGTH: 51
<212> TYPE: DNA
<213> ORGANISM: Unknown
<220> FEATURE:
<223> OTHER INFORMATION: Description of Unknown Organism: Synthetic oligonucleotide

<400> SEQUENCE: 5
gagtctcaga ctatctggag cgactgactc aaacttggtc tgacagttac c         51

<210> SEQ ID NO 6
<211> LENGTH: 40

```
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 6
gtaaatatcg gactctacaa tcaaatatgt atccgctcat                            40

<210> SEQ ID NO 7
<211> LENGTH: 82
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 7
gatcgagtct gacatcgagc gcctagcatt agtcagactc gatatcgagt ctcagcctgt      60
tagcgatggt acatgacgac tc                                              82

<210> SEQ ID NO 8
<211> LENGTH: 82
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 8
ctaggagtcg tcatgtacca tcgctaacag gctgagactc gatatcgagt ctgactaatg      60
ctaggcgctc gatgtcagac tc                                              82

<210> SEQ ID NO 9
<211> LENGTH: 22
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 9
catgtctaga ctgcagagat ct                                              22

<210> SEQ ID NO 10
<211> LENGTH: 18
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 10
agatctctgc agtctaga                                                   18

<210> SEQ ID NO 11
<211> LENGTH: 21
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 11
tacattcaaa tatgtatccg c                                               21
```

```
<210> SEQ ID NO 12
<211> LENGTH: 21
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 12
taaacttggt ctgacagtta c                                              21

<210> SEQ ID NO 13
<211> LENGTH: 54
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 13
gagtatccgc ttaggtcaat cggactcgga ccggatatca catgtgagtc gtca          54

<210> SEQ ID NO 14
<211> LENGTH: 54
<212> TYPE: DNA
<213> ORGANISM: Unknown
<220> FEATURE:
<223> OTHER INFORMATION: Description of Unknown Organism: Synthetic
      oligonucleotide

<400> SEQUENCE: 14
cctgttagcg atggtacatg acgactcaca tgtgatatcc ggtccgagtc cgat          54

<210> SEQ ID NO 15
<211> LENGTH: 10
<212> TYPE: DNA
<213> ORGANISM: N.BstNBI Recognition Sequence
<220> FEATURE:
<223> OTHER INFORMATION: N indicates any base (subject to the normal
      rules of base pairing between the strands).

<400> SEQUENCE: 15 gagtcnnnnn                                                           10

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 16
gcgtctaaac ccagatgt                                                  18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 17
gcgttcaaac ccagatgt                                                  18
```

```
<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 18
agctgttcta agccgcaa                                                   18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 19
tgtgaacacc tcgtaacg                                                   18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 20
ttcccaagca catgggat                                                   18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 21
tctccaagca cagtgagt                                                   18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 22
tgactcaagc gagtactc                                                   18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 23
tgactcaagc ggatactc                                                   18

<210> SEQ ID NO 24
```

```
<211> LENGTH: 18
<212> TYPE: DNA
<213> ORGANISM: Artificial Sequence
<220> FEATURE:
<223> OTHER INFORMATION: Description of Artificial Sequence: Theoretical
      sequences - all randomly generated

<400> SEQUENCE: 24
tgacctaagc ggatactc                                               18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 25
actgagcgcc atgcatta                                               18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 26
actgagcgcc agtcatta                                               18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 27
atcgagcgcc atgcatta                                               18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 28
atcgagcgcc tagcatta                                               18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 29
tgtaccatcg ctaacagg                                               18

<210> SEQ ID NO 30
<211> LENGTH: 36
```

```
<212> TYPE: DNA
<213> ORGANISM: Artificial Sequence
<220> FEATURE:
<223> OTHER INFORMATION: Description of Artificial Sequence: Theoretical
      sequence - implemented via the synthetic oligonucleotide, but
      never existed as independent entity

<400> SEQUENCE: 30
gagtctgaca tcgagcgcct agcattagtc agactc                              36

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Theoretical
      sequence - implemented via the synthetic oligonucleotide, but
      never existed as independent entity.

<400> SEQUENCE: 31
gagtccgatt gacctaagcg gatactctga cgactc                              36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Theoretical
      sequence - implemented via the synthetic oligonucleotide, but
      never existed as independent entity

<400> SEQUENCE: 32
gagtctcagc ctgttagcga tggtacatga cgactc                              36

<210> SEQ ID NO 33
<211> LENGTH: 50
<212> TYPE: DNA
<213> ORGANISM: synthetic oligonucleotide
<220> FEATURE:
<223> OTHER INFORMATION: N/A

<400> SEQUENCE: 33
gagtcagctc aatgttgcca gtcaggactc gtagaaaaga tcaaggatc                50

<210> SEQ ID NO 34
<211> LENGTH: 35
<212> TYPE: DNA
<213> ORGANISM: synthetic oligonucleotide
<220> FEATURE:
<223> OTHER INFORMATION: N/A

<400> SEQUENCE: 34
gggccacgta gactcgagca aaaggccagc aaaag                               35

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 35
gtagttacgc ca                                                        12

<210> SEQ ID NO 36
<211> LENGTH: 12
```

```
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 36
caatgttgcc ag                                                              12

<210> SEQ ID NO 37
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 37
tctcaatgag gc                                                              12

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 38
agcgagcctt ta                                                              12

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 39
tgatcgagac ct                                                              12

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 40
tctgcggata ac                                                              12

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 41
tatgcagcgc at                                                              12

<210> SEQ ID NO 42
<211> LENGTH: 12
<212> TYPE: DNA
```

```
<213> ORGANISM: Artificial Sequence
<220> FEATURE:
<223> OTHER INFORMATION: Description of Artificial Sequence: Theoretical
      sequence - randomly generated

<400> SEQUENCE: 42
gatcgaacgt tc                                                         12

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 43
aaatttgggc cc                                                         12

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 44
actatctgga gc                                                         12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 45
aggcgacatt tc                                                         12

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence: Theoretical
      sequence - randomly generated

<400> SEQUENCE: 46
atttacgggc ca                                                         12

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence:Theoretical
      sequence - implemented via the synthetic oligonucleotide, but
      never existed as independent entity.

<400> SEQUENCE: 47
gagtcagctc aatgttgcca gtcaggactc                                      30

<210> SEQ ID NO 48
<211> LENGTH: 30
<212> TYPE: DNA
```

```
<213> ORGANISM: Artificial Sequence
<220> FEATURE:
<223> OTHER INFORMATION: Description of Artificial Sequence: Theoretical
      sequence - implemented via the synthetic  oligonucleotide, but
      never existed as independent entity.

<400> SEQUENCE: 48
gagtccgata tttacgggcc acgtagactc                                          30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence:Theoretical
      sequence - implemented via the synthetic oligonucleotide, but
      never existed as independent entity.

<400> SEQUENCE: 49
gagtctcaga ctatctggag cgactgactc                                          30

<210> SEQ ID NO 50
<211> LENGTH: 48
<212> TYPE: DNA
<213> ORGANISM: Unknown
<220> FEATURE:
<223> OTHER INFORMATION: Description of Unknown Organism: Synthetic
      Oligonucleotide

<400> SEQUENCE: 50
ctggcaacat tgatcggact cggaccggat atcacatgtg agtcgtca                      48

<210> SEQ ID NO 51
<211> LENGTH: 48
<212> TYPE: DNA
<213> ORGANISM: Unknown
<220> FEATURE:
<223> OTHER INFORMATION: Description of Unknown Organism: Synthetic
      Oligonucleotide

<400> SEQUENCE: 51
gctccagata gttgacgact cacatgtgat atccggtccg agtccgat                      48
```